US012779025B2

(12) United States Patent
Izard et al.

(10) Patent No.: US 12,779,025 B2
(45) Date of Patent: Nov. 3, 2026

(54) METHODS AND COMPOSITIONS FOR ORALLY DOSING ANIMALS

(71) Applicant: Animal Science Products, Inc., Nacogdoches, TX (US)

(72) Inventors: Ryan Sylvester Izard, Nacogdoches, TX (US); Culley Keith Wilson, Nacogdoches, TX (US); Jessica Laurin Seate, Nacogdoches, TX (US); Serghei Barba, Nacogdoches, TX (US)

(73) Assignee: Animal Science Products, Inc., Nacogdoches, TX (US)

( * ) Notice: Subject to any disclaimer, the term of this patent is extended or adjusted under 35 U.S.C. 154(b) by 226 days.

(21) Appl. No.: 18/669,299

(22) Filed: May 20, 2024

(65) Prior Publication Data

US 2024/0382574 A1 Nov. 21, 2024

Related U.S. Application Data

(60) Provisional application No. 63/503,274, filed on May 19, 2023.

(51) Int. Cl.

| | |
|---|---|
| ***A61K 39/108*** | (2006.01) |
| ***A61K 9/00*** | (2006.01) |
| ***A61K 31/53*** | (2006.01) |
| *A61K 39/00* | (2006.01) |

(52) U.S. Cl.

CPC ........ *A61K 39/0258* (2013.01); *A61K 9/0056* (2013.01); *A61K 31/53* (2013.01); *A61K 2039/542* (2013.01); *A61K 2039/552* (2013.01)

(58) Field of Classification Search

CPC .. A61K 39/0258; A61K 9/0056; A61K 31/53; A61K 2039/542; A61K 2039/552

USPC .......................................................... 426/61

See application file for complete search history.

(56) References Cited

U.S. PATENT DOCUMENTS

| | | | | |
|---|---|---|---|---|
| 4,851,226 | A | 7/1989 | Julian et al. | |
| 5,075,114 | A | 12/1991 | Roche | |
| 5,876,759 | A | 3/1999 | Gowan, Jr. | |
| 7,494,669 | B2 | 2/2009 | Ni et al. | |
| 8,092,853 | B2 * | 1/2012 | Lanter ...................... | A61P 3/02 426/573 |
| 11,051,533 | B2 | 7/2021 | Lanter et al. | |
| 2015/0351428 | A1 * | 12/2015 | Izard ................... | A23K 20/184 424/234.1 |
| 2022/0117896 | A1 * | 4/2022 | Palmer ................... | A23K 50/75 |

FOREIGN PATENT DOCUMENTS

WO WO-2016135623 A1 † 9/2016

* cited by examiner
† cited by third party

*Primary Examiner* — Brent T O'Hern
(74) *Attorney, Agent, or Firm* — POLSINELLI PC

(57) ABSTRACT

Compositions and methods for administering an active ingredient to an animal are disclosed. The compositions comprise powder compositions that can be used to prepare gel compositions comprising active ingredients as well as gel compositions comprising the active ingredients. Methods of preparing the gel compositions and methods of administering the active ingredient to the animal are also disclosed.

5 Claims, 9 Drawing Sheets

| Score* | 0 | 1 | 2 | 3 |
|---|---|---|---|---|
| Description | No scour, normal solid feces in the crate. | Pasty feces in the crate. | Yellow liquid, opaque feces with few solid particles. | Yellow liquid, translucent, projectile feces. |
| Examples |  |  |  [3]  |  [3] |

* The most severe puddle that you see, is the score that is given for that crate

METHODS AND COMPOSITIONS FOR ORALLY DOSING ANIMALS

CROSS REFERENCE TO RELATED APPLICATIONS

This application claims priority to U.S. Provisional Patent Application Ser. No. 63/503,274, filed May 19, 2023, and titled "METHODS AND COMPOSITIONS FOR ORALLY DOSING ANIMALS" which is incorporated by reference herein in its entirety.

FIELD OF THE INVENTION

Gel and powder compositions and methods for administering an active ingredient to an animal are disclosed.

BACKGROUND OF THE INVENTION

New tools for improving pig health are being added to traditional management methods at a quickening pace. Orally active products like live vaccines to increase natural immunity, probiotic bacteria, and prebiotic carbohydrates to outcompete gut pathogens, antibody proteins to bind disease antigens, and targeted nutrients to enhance early gut development seem to be introduced daily. What has not improved is the delivery mechanism for beneficial oral products. Until now, oral delivery meant catching pigs and forcibly dosing with some combination of syringes, pump bottles, and drench guns. Accordingly, there is a need for compositions and methods of delivering orally active products safely, effectively, and efficiently to animals without dosing tools.

SUMMARY OF THE INVENTION

One aspect of the instant disclosure encompasses a powder composition for oral administration of an active ingredient to an animal. The composition comprises a gelling agent; a gel activator; an antioxidant; a buffering agent; and an electrolyte.

One aspect of the disclosure encompasses a method for preparing a therapeutic gel composition for oral administration of an active ingredient to an animal, the method comprising solubilizing an amount of a powder composition in a volume of water to form a gelling solution wherein the powder composition comprises a gelling agent, a gel activator, an antioxidant, a buffering agent, and an electrolyte. The method further comprises concomitantly or subsequently mixing an active ingredient with the gel solution and allowing a period of time for the gelling solution to form a gel.

The disclosure further encompasses a method of orally administering an active ingredient to an animal in need thereof, the method comprising: preparing or having prepared a therapeutic gel composition disclosed herein; and feeding the animal the gel composition, thereby administering the active ingredient to the animal. In some aspects, orally administering an active ingredient to an animal comprises feeding an effective amount of the therapeutic gel composition to the animal.

In a specific aspect, the disclosure further comprises a method of vaccinating an animal. The method comprises preparing a vaccine composition by solubilizing an amount of a powder composition in a volume of water to form a gelling solution, wherein the powder composition comprises a gelling agent, a gel activator, an antioxidant; a buffering agent, and an electrolyte. The method further comprises concomitantly or subsequently mixing a vaccine with the gel solution to form a vaccine composition and feeding the vaccine composition to the animal, thereby vaccinating the animal. In some aspects, vaccinating an animal comprises feeding an effective amount of the vaccine composition to the animal.

In one aspect of the method, the gelling agent of the powder composition is sodium alginate. In yet another aspect, the gel activator of the powder composition is dicalcium phosphate, calcium carbonate, calcium gluconate, calcium iodate, calcium oxide, calcium sulfate, or any combination thereof. In further aspect, the antioxidant of the powder composition is sodium thiosulfate. The buffering agent of the powder composition of the method disclosed herein, can be disodium phosphate, monopotassium phosphate, and sodium bicarbonate, and the electrolyte of the powder composition is sodium chloride and potassium chloride.

In one aspect, the period of time of the method disclosed herein is about 1 minute to about 10 minutes.

In certain aspects, the powder composition comprises a composition of Table 1. In further aspects, the powder composition is solubilized at a rate of about 400 to about 500 g in one gallon of water or about 125 g to about 135 g of the dry powder in one liter of water.

In some aspects of the method, the active ingredient is selected from the group consisting of a live vaccine, a probiotic, a prebiotic, an antibody protein, a targeted nutrient, an antiparasitic, a coccidiostat, a pain medication, a pheromone, and any combination thereof. In certain aspects, the active ingredient is selected from the group consisting of toltrazuril, a *Lactobacillus* strain, meloxicam, a vaccine, and any combination thereof. In yet another aspect, the vaccine is selected from the group consisting of a *Salmonella* spp. vaccine, an *E. coli* vaccine, an Erysipelas vaccine, a *Lawsonia* (ileitis) vaccine, and any combination thereof.

Other aspects and iterations of the invention are described more thoroughly below.

BRIEF DESCRIPTION OF THE SEVERAL VIEWS OF THE DRAWINGS

The following drawings form part of the present specification and are included to further demonstrate certain embodiments of the present disclosure. Certain embodiments can be better understood by reference to one or more of these drawings in combination with the detailed description of specific embodiments presented herein.

DETAILED DESCRIPTION

Figure 1:
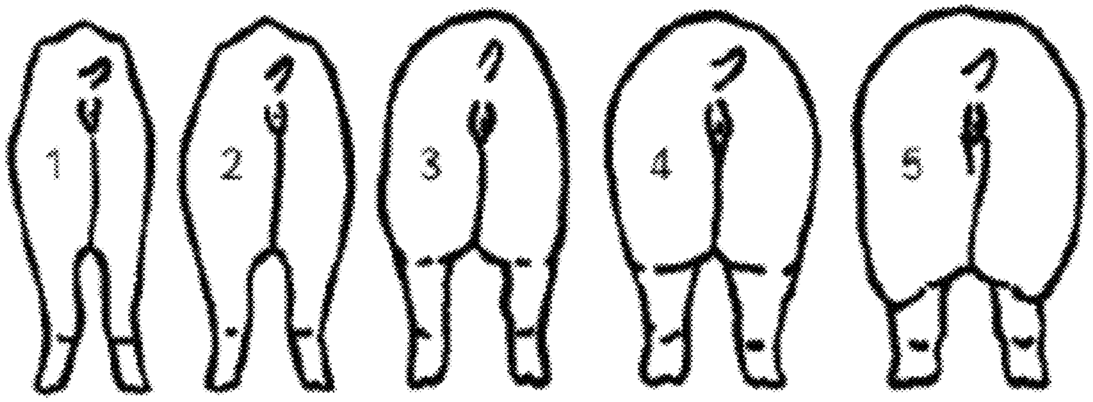
FIG. 1 is a schematic of sow visual body condition scoring criteria. Scoring criteria are shown in Table 3.

The present disclosure encompasses gel compositions or powder compositions for preparing the gel compositions, and methods of using the gel compositions to orally administer active ingredients such as delicate vaccines and probiotics to animals, in particular pigs. The compositions and methods of the disclosure provide means to deliver active ingredients orally without resorting to traditional methods of administering to animals using dosing tools. For example, in the case of the delicate Erysipelas vaccine, managers can immunize pigs by simply mixing the oral Erysipelas vaccine in a gel made from the farm's own tap water and a dry composition of the disclosure to form an edible gel and feeding the resulting gel to the animal without the need for catching the animals or using dosing tools. The compositions and methods of the instant disclosure provide at least the following advantages. The gel compositions provide a means to orally deliver active ingredients without resorting to traditional methods of administering to animals using dosing tools partly because the compositions buffer both acidic and alkaline pH levels to neutral; neutralize harmful effects of chlorine and other oxidizers in tap water; balance tonicity for optimal electrolyte balance and ensures uniform suspension ideal for insoluble ingredients. The dry compositions are easy to hydrate and homogenize to form a gel formulation at the farm using farm equipment and water. The gel is highly palatable and readily consumed by animals.

I. Powder and Gel Compositions

One aspect of the instant disclosure encompasses a dry powder composition for oral administration of an active ingredient to an animal. The composition comprises a gelling agent and a gel activator. The composition can further comprise an antioxidant, a buffering agent, an electrolyte, and any combination thereof. In some aspects, the composition comprises a gelling agent, a gel activator, a buffering agent, an antioxidant, and an electrolyte. In some aspects, the composition of the present disclosure further comprises feed nutrient components, additives, or both. In some aspects, the composition of the present disclosure is free of feed nutrient components. In some aspects, the composition of the present disclosure is free of feed additives. The gelling agent, gel activator, buffering agent, and electrolyte are described herein further below.

(a) Gelling Agent

The gelling agent of the instant disclosure is responsible for the formation of a gel-like substance when the powder is mixed with a liquid. The gelling agent can be any suitable consumable material capable of forming a gel, such as natural or synthetic polymers, hydrocolloids, or gelling clays. In some aspects, gelling agents of the instant disclosure are suitable for oral administration to animals.

An edible gel is a semi-solid material that is capable of retaining its shape due to the presence of a three-dimensional network of long-chain molecules (polymers) that trap liquid or gas within them. The gel can be made from a variety of ingredients, including proteins, carbohydrates, or synthetic polymers, and is often used as a thickener, stabilizer, or gelling agent in food products. It is important to note that the choice of gelling agent will depend on factors like the desired texture, strength, stability, and taste of the final product, as well as any other requirements that need to be considered such as dietary restrictions, allergens, and any effect the gelling agent may have on an active ingredient to be used in the gel.

Gel strength refers to the ability of an edible gel to resist deformation under mechanical stress, such as squeezing, cutting, or bending. The strength of the gel depends on several factors, such as the type and concentration of the gelling agent, the temperature, and the pH of the gel. Gel strength is commonly measured using a texture analyzer, which applies a controlled force to the gel and measures the deformation of the gel under that force. One method of measuring gel strength is the Bloom test. In this test, a sample of gelatin is placed in a cylindrical container and allowed to set. A plunger of a specific size and weight is then lowered onto the surface of the gel, and the force required to make a depression of a certain depth is measured in grams. The higher the Bloom value, the stronger the gelatin gel. Other methods of measuring gel strength include the penetration test, in which a needle is used to measure the force required to penetrate the gel, and the oscillation test, in which the gel is subjected to a sinusoidal force, and the response of the gel is measured using a rheometer.

Non-limiting examples of consumable polymer gelling agents suitable for a composition of the instant disclosure include alginate, carrageenan, gelatin, guar gum, xanthan gum, chitosan, pectin, konjac glucomannan, agar, gellan gum, tara gum, carboxymethyl cellulose (CMC), locust bean gum, polyvinyl alcohol (PVA), or any combination thereof.

In some aspects, the gelling agent is alginate. Alginate is a natural polymer derived from seaweed that is commonly used in food and pharmaceuticals. Alginate can form a gel when it comes into contact with a gel activator such as divalent cations which can crosslink the polymer chains. Calcium ion containing compounds are commonly used gel activators for alginate gels. The strength of the resulting gel depends on the concentration of alginate and the concentration of the divalent cations. In some aspects, the ion containing compound is calcium chloride. For example, when the ion containing compound is calcium chloride, at 1% alginate concentration, the gel strength is around 500 g/cm$^2$ with 0.05 M calcium chloride, while at 2% alginate concentration, the gel strength can be as high as 800 g/cm$^2$ with 0.2 M calcium chloride.

In some aspects, the natural gelling agent is carrageenan. Carrageenan is a highly branched polysaccharide extracted from red seaweed and often used in dairy products, meat, and pet food. Carrageenan can form a gel when it comes into contact with potassium ions, which can crosslink the polymer chains. Potassium chloride is commonly used as a gel activator for carrageenan gels. The strength of the resulting gel depends on the concentration of carrageenan and the concentration of potassium ions. For example, at 0.5% carrageenan concentration, the gel strength is around 20 g/cm$^2$ with 0.1 M potassium chloride, while at 1% carrageenan concentration, the gel strength can be as high as 100 g/cm$^2$ with 0.3 M potassium chloride.

In some aspects, the natural gelling agent is gelatin. Gelatin is a protein derived from collagen in animal skin, bones, and connective tissue, and widely used in food, pharmaceuticals, and personal care products. Gelatin can form a gel when it is heated and then cooled. The strength of the resulting gel depends on the concentration of gelatin and the temperature at which it is set. For example, at 6% gelatin concentration, the gel strength is around 200 g/cm$^2$ when the gel is set at 10° C., while at 12% gelatin concentration, the gel strength can be as high as 700 g/cm$^2$ when the gel is set at 4° C.

In some aspects, the natural gelling agent is guar gum. Guar gum is a water-soluble natural polymer derived from the guar bean and commonly found in food and personal care products. Guar gum can form a gel when it comes into contact with water, and its gelling properties can be enhanced by the addition of borax or other crosslinking agents. The strength of the resulting gel depends on the concentration of guar gum and the concentration of crosslinking agent. For example, at 0.5% guar gum concentration, the gel strength is around 200 g/$cm^2$ with 0.02% borax, while at 1% guar gum concentration, the gel strength can be as high as 400 g/$cm^2$ with 0.04% borax.

In some aspects, the natural gelling agent is ghatti gum. Ghatti gum is a natural polymer derived from the exudates of the *Anogeissus latifolia* tree, and used as a thickening, stabilizing, and emulsifying agent in food, pharmaceutical, and cosmetic products. Ghatti gum can form a gel when it comes into contact with water, and its gelling properties can be enhanced by the addition of borax or other crosslinking agents. The strength of the resulting gel depends on the concentration of ghatti gum and the concentration of crosslinking agent. For example, at 0.5% ghatti gum concentration, the gel strength is around 60 g/$cm^2$ with 0.1% borax, while at 1% ghatti gum concentration, the gel strength can be as high as 150 g/$cm^2$ with 0.2% borax.

In some aspects, the natural gelling agent is tara gum. Tara gum is a natural polymer extracted from the seeds of the *Caesalpinia spinosa* tree and used as a thickening and gelling agent in food and pharmaceutical products. Tara gum can form a gel when it comes into contact with water, and its gelling properties can be enhanced by the addition of calcium or other crosslinking agents. The strength of the resulting gel depends on the concentration of tara gum and the concentration of crosslinking agent. For example, at 0.5% tara gum concentration, the gel strength is around 60 g/$cm^2$ with 0.1% calcium chloride, while at 1% tara gum concentration, the gel strength can be as high as 150 g/$cm^2$ with 0.2% calcium chloride.

In some aspects, the natural gelling agent is CMC. CMC is a modified cellulose polymer that can be synthesized from natural cellulose fibers, and used as a thickening, stabilizing, and gelling agent in food, pharmaceutical, and personal care products. CMC can form a gel when it comes into contact with water, and its gelling properties can be enhanced by the addition of borax or other crosslinking agents. The strength of the resulting gel depends on the concentration of CMC and the concentration of crosslinking agent. For example, at 0.5% CMC concentration, the gel strength is around 40 g/$cm^2$ with 0.2% borax, while at 1% CMC concentration, the gel strength can be as high as 80 g/$cm^2$ with 0.4% borax.

In some aspects, the natural gelling agent is locust bean gum. Locust bean gum is a natural polymer extracted from the seeds of the carob tree, and used as a thickening, stabilizing, and gelling agent in food, pharmaceutical, and cosmetic products. Locust bean gum can form a gel when it comes into contact with water, and its gelling properties can be enhanced by the addition of calcium or other crosslinking agents. The strength of the resulting gel depends on the concentration of locust bean gum and the concentration of crosslinking agent. For example, at 0.5% locust bean gum concentration, the gel strength is around 70 g/$cm^2$ with 0.1% calcium chloride, while at 1% locust bean gum concentration, the gel strength can be as high as 150 g/$cm^2$ with 0.2% calcium chloride.

In some aspects, the natural gelling agent is xanthan gum. Xanthan gum is a polysaccharide produced from the fermentation of glucose, sucrose, or lactose by the *Xanthomonas campestris* bacterium, and often used in food, pharmaceuticals, and personal care products. Xanthan gum can form a gel when it comes into contact with water, and its gelling properties can be enhanced by the addition of a gel activator such as calcium or other divalent cations. The strength of the resulting gel depends on the concentration of xanthan gum and the concentration of gel activator. For example, at 0.5% xanthan gum concentration, the gel strength is around 30 g/$cm^2$ with 0.1% calcium chloride, while at 1% xanthan gum concentration, the gel strength can be as high as 70 g/$cm^2$ with 0.2% calcium chloride.

In some aspects, the natural gelling agent is chitosan. Chitosan is derived from chitin, a natural polymer found in the shells of crustaceans, and often used in dietary supplements and biomedical applications. Chitosan can be used as a gelling agent, and its gelling properties are influenced by several factors such as pH, temperature, concentration, and the presence of ions or other additives. Chitosan gels can be formed by adjusting the pH to around 4.5, which causes chitosan to become positively charged and able to form cross-links with other chitosan molecules. The addition of a gel activator, such as a polyanionic compound like sodium tripolyphosphate, can further enhance the gelling properties of chitosan. The gel strength of chitosan gels can vary depending on the concentration of chitosan, with higher concentrations resulting in stronger gels. For example, at a chitosan concentration of 1%, the gel strength can be around 500 g/$cm^2$, while at a concentration of 2%, the gel strength can increase to around 1500 g/$cm^2$.

In some aspects, the natural gelling agent is pectin. Pectin is a natural polymer derived from fruits, particularly citrus fruits, and commonly used in food and pharmaceuticals. Pectin is widely used as a gelling agent in the food industry, and its gelling properties are influenced by several factors such as pH, sugar concentration, and the presence of calcium ions. Pectin gels can be formed by dissolving pectin in a hot liquid and then cooling the mixture, which allows pectin to form cross-links and create a gel network. The addition of a gel activator, such as calcium ions, can further enhance the gelling properties of pectin. The strength of the resulting pectin gel depends on the concentration of pectin and the concentration of gel activator. For example, at a pectin concentration of 0.5%, the gel strength can be around 50 g/$cm^2$ with 0.1% calcium ions, while at a concentration of 1%, the gel strength can increase to around 150 g/$cm^2$ with 0.2% calcium ions.

In some aspects, the natural gelling agent is konjac glucomannan. Konjac glucomannan is a water-soluble polysaccharide extracted from the corm of the konjac plant and commonly found in food and dietary supplements. Konjac glucomannan is commonly used as a gelling agent in food, pharmaceutical, and personal care products due to its high viscosity and gel-forming properties. Konjac glucomannan can form a gel when it comes into contact with water, and its gelling properties can be enhanced by the addition of a gel activator such as calcium or other divalent cations. The strength of the resulting konjac glucomannan gel depends on the concentration of konjac glucomannan and the concentration of gel activator. For example, at a concentration of 0.5%, the gel strength can be around 40 g/$cm^2$ with 0.1% calcium chloride, while at a concentration of 1%, the gel strength can increase to around 80 g/$cm^2$ with 0.2% calcium chloride. The gelling properties of konjac glucomannan are also affected by the pH and temperature of the solution, with higher pH and temperature resulting in weaker gels.

In some aspects, the natural gelling agent is agar. Agar is a natural polymer extracted from red algae and often used in food and microbiology. Agar can form a gel when it is dissolved in hot water and allowed to cool, without the need for a gel activator. The strength of the resulting agar gel depends on the concentration of agar and the cooling rate of the solution. For example, at a concentration of 1%, the gel strength can be around 200 g/$cm^2$ with a cooling rate of 2° C./min, while at a concentration of 2%, the gel strength can increase to around 400 g/$cm^2$ with the same cooling rate.

The gelling properties of agar are also affected by the pH and temperature of the solution, with higher pH and temperature resulting in weaker gels. Additionally, agar gels can be liquefied by heating the gel to around 85° C., and they can be re-gelled by cooling the solution again.

In some aspects, the natural gelling agent is gellan gum. Gellan gum is a water-soluble polysaccharide produced by the bacterium *Sphingomonas elodea* and often used in food, personal care products, and pharmaceuticals. Gellan can form a gel when it is dissolved in hot water and allowed to cool, and its gelling properties can be enhanced by the addition of a divalent cation such as calcium or magnesium ions. The strength of the resulting gellan gel depends on the concentration of gellan and the concentration of gel activator. For example, at a concentration of 0.5%, the gel strength can be around 50 $g/cm^2$ with 0.1% calcium ions, while at a concentration of 1%, the gel strength can increase to around 150 $g/cm^2$ with 0.2% calcium ions. Gellan gels are also stable over a wide range of temperatures and pH values, and they can withstand freeze-thaw cycles without losing their gelling properties. Additionally, gellan can also form fluid gels and suspensions, which makes it useful in a variety of food and beverage applications.

(b) Activators/Gelling Enhancers

Natural polymer cross-linkers, also called gel activators or gelling enhancers, are compounds that are added to gelling agents to enhance their gelling properties. In some aspects, natural gelling agent cross-linkers are an important component of gelling systems, and they can be used to create a wide range of gels with different properties and textures. By selecting the type and concentration of cross-linker, it is possible to create gels with specific functionalities that can be tailored to different applications in the food, pharmaceutical, and biomedical industries.

In some aspects, cross-linkers work by creating chemical bonds between the polymer chains, which results in a stronger and more stable gel. Some examples of natural polymer cross-linkers include calcium ions, magnesium ions, potassium ions, and borate ions. These ions can form ionic bonds with the charged groups on the polymer chains, resulting in a 3D network that traps water and creates a gel. Proteins can also act as natural cross-linkers due to their ability to form disulfide bonds, hydrogen bonds, and other types of chemical interactions with other molecules. For example, transglutaminase is an enzyme that can cross-link protein molecules, creating a stronger and more stable gel network. Some polysaccharides, like pectin, contain natural crosslinking groups, while others, like chitosan, can be cross-linked using external agents like genipin or sodium tripolyphosphate. Polyphenols are naturally occurring compounds found in many plants, including fruits, vegetables, and spices. They can act as cross-linkers by forming covalent bonds with proteins and other polymers. For example, tannins are polyphenols that can cross-link proteins, creating astringent and stable gels.

In some aspects, the concentration range of cross-linkers used for gelling depends on the type of polymer and the desired strength of the gel. For example, calcium ions are commonly used as a cross-linker for alginate, with a concentration range of 0.5-2% usually used for gelling. Similarly, borate ions are commonly used as a cross-linker for pectin, with a concentration range of 0.05-0.2% typically used for gelling. The concentration range of cross-linkers can also affect the texture and rheological properties of the resulting gel, with higher concentrations resulting in a firmer and more rigid gel.

In some aspects, the gel activator of the instant disclosure comprises calcium ions. Non-limiting examples of calcium ion activators include dicalcium phosphate, calcium carbonate, calcium gluconate, calcium iodate, calcium oxide, calcium sulfate or any combination thereof. In some aspects, the gel activator is calcium sulfate.

(c) Other Ingredients

In some aspects, compositions of the instant disclosure can further comprise additional ingredients that can contribute to properties of the compositions. For instance, buffering agents and electrolytes can be used to enhance flavor and texture, as well as to insulate an active ingredient such as a vaccine from changes (e.g., oxidation, variable pH, and electrolyte balance).

It will be noted that many ingredients used in consumable products and products with active ingredients such as vaccines, probiotics, and drugs can perform multiple functions. This can be desirable as it allows for more efficient and effective product development, manufacturing, and use. For instance, phosphates can be used as buffering agents and electrolytes. This is because phosphates contain charged particles that can conduct electrical current in a solution, making them essential for maintaining proper cellular function and hydration in the body. As a result, phosphates can be commonly used in consumable products such as sports drinks, electrolyte-enhanced water, and oral rehydration solutions.

Vitamin C can also perform multiple functions. In addition to its role as an antioxidant, vitamin C also plays a critical role in immune function, wound healing, and collagen synthesis. It can be added to consumable products and drugs to enhance their nutritional value and promote overall health. In vaccines, adjuvants are often used to enhance the immune response to the active ingredient. Adjuvants can perform multiple functions, such as stabilizing the active ingredient, promoting uptake by immune cells, and enhancing the duration and intensity of the immune response. As a result, adjuvants can improve the efficacy and safety of vaccines, reducing the risk of infectious diseases.

A. Buffering Agents

In some aspects, the composition of the instant disclosure comprises a buffering agent. Buffering agents are chemical compounds that are added to consumables, such as food and beverages, to maintain a stable pH level. Changes in pH can affect the taste, texture, and stability of the product. Buffering agents can also increase the shelf life of the consumable by preventing spoilage and degradation and provide a stable pH environment for a delicate active ingredient such as a vaccine. It will be recognized that it is important to use buffering agents in the correct amounts and combinations, as excessive amounts or inappropriate combinations can lead to negative effects on the product's sensory properties or even pose a health risk to an animal consuming a product. Accordingly, a selection of buffering agents for an intended composition is carefully considered when used in consumables to ensure product safety, quality, and active ingredient stability.

The pH range normally found in consumable products varies widely depending on the type of product and its intended use. Generally, the pH of consumable products falls within a narrow range to ensure safety, palatability, and stability of the product. For instance, most foods and beverages have a pH range between 4.5 and 7.5. However, in some aspects, such as in soft drinks, fruit juices, and sports drinks a pH can range between 2.5 and 4.5. Bakery products such as bread, cakes, and cookies can have a pH range between 6.0 and 8.0. The pH of meat and poultry products can vary widely depending on the processing method but can fall within a range between 5.5 and 7.5.

The pH of orally administered active ingredients such as vaccines, probiotics, and drugs is an important consideration for their efficacy and safety. For vaccines, the pH of a solution can affect the stability and efficacy of the vaccine. Vaccines can have a pH range of 6.0 to 7.5, which is close to the pH of the human body. The pH of the vaccine solution can be carefully monitored during production, storage, and preparation for administration to ensure that a vaccine or other active ingredients remain effective and safe for use. Probiotics, which are live bacteria that are ingested for their health benefits, are also affected by pH. The pH of the gastrointestinal tract can influence the survival and effectiveness of the probiotics. Probiotics are typically designed to survive the acidic environment of the stomach and reach the intestines, where they can provide health benefits. The pH of the probiotic supplement can be adjusted to optimize its survival and effectiveness. For drugs, the pH of the solution can affect the solubility and stability of the drug. The pH of the drug solution can also affect its absorption and distribution in the body. The pH of the drug solution can be carefully selected to ensure that the drug is stable and effective in the body.

Non-limiting examples of buffering agents used in consumables include phosphates, carbonates, citrates, tris buffers, and buffered saline salts (e.g., Tris buffered saline or phosphate buffered saline), one or more salts of each, or any combination thereof.

In some aspects, the buffering agent of the instant disclosure is a phosphate buffering agent or any combination of phosphate buffering agents. Non-limiting examples of phosphate buffering agents suitable for a composition of the instant disclosure include sodium phosphate—a type of buffering agent that is made up of a combination of phosphoric acid and sodium hydroxide; sodium phosphate which can be found in a variety of food products, including processed meats, cheese, and baked goods; potassium phosphate—a type of buffering agent that is made up of a combination of phosphoric acid and potassium hydroxide; potassium phosphate—commonly used in dietary supplements and as a pH adjuster in food and beverage products; calcium phosphate—a type of buffering agent that is made up of a combination of phosphoric acid and calcium hydroxide; calcium phosphate—commonly used as a dietary supplement and as a pH adjuster in food and beverage products; ammonium phosphate—a type of buffering agent that is made up of a combination of phosphoric acid and ammonia; or any combination thereof. It will be noted that excessive consumption of phosphate-containing foods or supplements can be harmful to health, so these buffering agents are used in moderation and in compliance with regulatory guidelines. In some aspects, the buffering agent comprises disodium phosphate.

In some aspects, the buffering agent of the instant disclosure is a carbonate buffering agent or any combination of carbonate buffering agents. Non-limiting examples of carbonate buffering agents suitable for a composition of the instant disclosure include sodium carbonate—a white, odorless powder that is commonly used as a pH adjuster in food and beverages, as well as a cleaning agent in household and industrial applications; sodium bicarbonate—also known as baking soda, is a white crystalline powder that is commonly used as a leavening agent in baked goods, as well as a pH adjuster in food and beverages; potassium carbonate—a white, odorless powder that is commonly used as a pH adjuster in food and beverages, as well as a fertilizer in agriculture; calcium carbonate—a white, odorless powder that is commonly used as a dietary supplement, as well as a pH adjuster in food and beverages; magnesium carbonate—a white, odorless powder that is commonly used as a dietary supplement, as well as a pH adjuster in food and beverages; aluminum carbonate—a white, odorless powder that is commonly used as an antacid to relieve symptoms of heartburn and indigestion; or any combination thereof. In some aspects, the buffering agent comprises sodium bicarbonate.

In some aspects, the buffering agent of the instant disclosure comprises disodium phosphate and sodium bicarbonate.

B. Electrolytes

In some aspects, a composition of the instant disclosure comprises electrolytes. Electrolytes are charged particles that can conduct electrical current in a solution. In the context of consumable products and active ingredients such as vaccines, probiotics, and drugs, electrolytes play an important role in maintaining proper pH balance, hydration, and cellular function in the body. Electrolytes are commonly used in consumable products such as sports drinks and electrolyte-enhanced water to help maintain proper hydration and replace electrolytes lost through sweating during exercise or other physical activity. Electrolytes such as sodium, potassium, and chloride are particularly important for farm animals, as they help maintain hydration, support muscle function, and aid in digestion. In addition, electrolytes can help prevent heat stress and dehydration in animals, particularly during hot weather or times of increased physical activity. Therefore, it is important for farmers to provide their animals with adequate amounts of electrolytes through their feed or water to maintain their overall health and performance.

In vaccines, electrolytes can be added to a vaccine solution to help stabilize the active ingredients and maintain their efficacy. Vaccines typically contain a combination of salts and sugars, including sodium chloride, potassium phosphate, and sucrose. These electrolytes help to maintain the stability of the vaccine during storage and transportation, ensuring that the vaccine remains effective when administered to patients.

Probiotics also require the presence of electrolytes to maintain their viability and effectiveness. The pH and electrolyte composition of the gastrointestinal tract can influence the survival and effectiveness of the probiotics. Therefore, probiotic supplements can contain electrolytes such as magnesium, calcium, and potassium to ensure their survival and effectiveness in the body.

For drugs, electrolytes can play an important role in the solubility, stability, and absorption of the drug in the body. Electrolytes such as sodium, potassium, and chloride may be added to drug formulations to enhance the solubility and absorption of the drug. The addition of electrolytes can also help to stabilize the drug and prevent it from degrading over time.

A wide range of electrolytes can be used in consumables and orally administered vaccines, probiotics, and drugs to promote proper cellular function, hydration, and health benefits. The selection and concentration of electrolytes in these products can be carefully considered to optimize their performance and minimize any potential adverse effects.

Non-limiting examples of electrolytes suitable for use in consumable compositions of the instant disclosure include sodium, potassium, chloride, magnesium, and calcium. Additional, non-limiting examples of electrolytes suitable for a composition of the instant disclosure include phosphates which are commonly used as buffering agents in consumables and are also used in vaccines to stabilize the active ingredients; bicarbonates which can be used as buffering agents in consumables to help maintain proper pH balance in the body and in vaccines and drugs to enhance the solubility and absorption of the active ingredients; iron, an essential mineral that plays a critical role in hemoglobin production and oxygen transport in the body and that can be added to consumables and drugs to enhance their nutritional value; zinc—an essential mineral that plays a role in immune function, wound healing, and protein synthesis and can be added to consumables and drugs to enhance their nutritional value; copper—essential mineral that plays a role in the formation of red blood cells, immune function, and collagen synthesis, and can be added to consumables and drugs to enhance their nutritional value; fluoride—commonly added to drinking water and toothpaste to promote dental health, and can be added to consumables and drugs to enhance their health benefits; chlorate which can be used as a disinfectant and can be added to drinking water and other consumables to reduce the risk of bacterial contamination sulfates; which are commonly used as a laxative and can be added to consumables and drugs to promote bowel movements.

In some aspects, an electrolyte of the instant disclosure comprises sodium chloride. In some aspects, an electrolyte of the instant disclosure comprises potassium chloride. In some aspects, an electrolyte of the instant disclosure comprises sodium chloride and potassium chloride.

C. Antioxidants

Several antioxidants can be used in formulations to protect delicate active ingredients such as vaccines from degradation due to oxidative stress during storage, transport, and handling. Non-limiting examples of antioxidants suitable for compositions of the instant disclosure include catalase, superoxide dismutase, ascorbic acid (vitamin C), alpha-tocopherol (vitamin E), glutathione, sodium bisulfite, sodium metabisulfite, sodium thiosulfate, butylated hydroxyanisole (BHA), butylated hydroxytoluene (BHT), propyl gallate, ethylenediaminetetraacetic acid (EDTA), mannitol, trehalose, polysorbate 80, dextrose, citric acid or any combination thereof. These antioxidants work by either scavenging free radicals or by helping to regenerate other antioxidants that have been depleted by oxidative stress. In some aspects, an antioxidant of the instant disclosure comprises sodium thiosulfate.

D. Excipients

Compositions of various aspects of the instant disclosure can comprise one or more excipients in addition to the ingredients described herein in Sections I (b) and (c). Non-limiting examples of excipients include binders, diluents (fillers), disintegrants, effervescent disintegration agents, preservatives (antioxidants), flavor-modifying agents, lubricants and glidants, dispersants, coloring agents, chelating agents, antimicrobial agents, release-controlling polymers, and any combination of any of these agents.

i. Binders

Non-limiting examples of binders suitable for compositions of the instant disclosure include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohols, polyethylene glycol, polyols, saccharides, oligosaccharides, polypeptides, oligopeptides, and any combination thereof.

ii. Diluent

Non-limiting examples of diluents (also referred to as “fillers” or “thinners”) include carbohydrates, inorganic compounds, and biocompatible polymers, such as polyvinylpirrolydone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing. Further examples of biocompatible polymers which are suitable for use as diluents in pharmaceutical formulations are described at Section I(a) herein above.

iii. Disintegrants

Disintegrants can be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Suitable effervescent disintegrants include but are not limited to sodium bicarbonate in combination with citric acid, and sodium bicarbonate in combination with tartaric acid.

iv. Preservatives

Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)- mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or any combination thereof. In an exemplary embodiment, the preservative is an antioxidant, such as a-tocopherol or ascorbate, and antimicrobials, such as parabens, chlorobutanol or phenol.

v. Flavor-Modifying Agents

Suitable flavor-modifying agents include flavorants, taste-masking agents, sweeteners, and the like. Flavorants include, but are not limited to, synthetic flavor oils and flavoring aromatics and/or natural oils, extracts from plants, leaves, flowers, fruits, and any combination thereof. Other non-limiting examples of flavors include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

Taste-masking agents include but are not limited to cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol copolymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking agents contemplated are those described in U.S. Pat. Nos. 4,851,226, 5,075,114, and 5,876,759, each of which is hereby incorporated by reference in its entirety.

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

vi. Lubricants and Glidants

The lubricant compositions can be utilized to lubricate ingredients that form a pharmaceutical composition. As a glidant, the lubricant facilitates removal of solid dosage forms during the preparation of a gel composition of the instant disclosure. Non-limiting examples of lubricants and glidants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil.

vii. Dispersants

Dispersants can include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

viii. Colorants

Depending upon the aspects, it can be desirable to include a coloring agent. Suitable color additives include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants can be suitable for use in various embodiments.

ix. Chelating Agents

A chelating agent can be included as an excipient to immobilize oxidative groups, including but not limited to metal ions, in order to inhibit the oxidative degradation of the morphinan by these oxidative groups. Non-limiting examples of chelating agents include lysine, methionine, glycine, gluconate, polysaccharides, glutamate, aspartate, and disodium ethylenediaminetetraacetate (Na2EDTA).

x. Antimicrobial Agents

An antimicrobial agent can be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, Na2EDTA, and sulfites including but not limited to sulfur dioxide, sodium bisulfite, and potassium hydrogen sulfite.

xi. Release-Controlling Polymers

Release-controlling polymers can be included in the various aspects of the compositions of the instant disclosure. Suitable release-controlling polymers include but are not limited to hydrophilic polymers and hydrophobic polymers. Suitable hydrophilic release-controlling polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, crosslinked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabicgum, carrageensgum, ghaftigum, guargum, karayagum, locust beangum, okragum, tragacanthgum, scleroglucangum, xanthangum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylamides, polyacrylic acid, polyamides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and any combination thereof.

xii. Essential Oils

There are many essential oils that are used in various industries, including food and beverage. Non-limiting examples of essential oils that can be used in edible compositions include peppermint oil, lemon oil, orange oil, cinnamon oil, clove oil, ginger oil, rosemary oil, lavender oil, thyme oil, basil oil, or any combination thereof. essential oils can be used in a variety of ways in edible compositions, including flavoring baked goods, seasoning meat dishes, and adding a burst of flavor to beverages. It is important to note that when using essential oils in food, a little goes a long way, and it is important to follow recommended guidelines for safe consumption.

xiii. Feed Supplements

The term “feed supplement” as used herein can refer to any feed composition normally fed to an animal. A feed supplement composition can and will vary depending on the animal, the composition in which the supplement is used, the intended use of a composition comprising the feed supplement among other variables. Animals can be as described in Section II herein below. Non-limiting examples of a dietary supplement can be a vitamin, mineral, amino acid, antioxidant, essential fatty acid, or any combination thereof. Suitable examples of each additional component are detailed below.

xiv. Vitamins

Non-limiting examples of suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The dietary supplement can include one or more forms of an effective amount of any of the vitamins described herein or otherwise known in the art. Exemplary vitamins include vitamin K, vitamin D, vitamin C, and biotin. An “effective amount” of a vitamin typically quantifies an amount at least about 10% of the United States Recommended Daily Allowance (“RDA”) of that particular vitamin for a subject. It is contemplated, however, that amounts of certain vitamins exceeding the RDA may be beneficial for certain subjects. For example, the amount of a given vitamin may exceed the applicable RDA by 100%, 200%, 300%, 400%, 500% or more.

xv. Minerals

In addition to the metal chelates or metal salts described in Section IA, the dietary supplement may include one or more minerals or mineral sources. Non-limiting examples of minerals include, without limitation, clay minerals, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and any combination thereof.

xvi. Essential Fatty Acids

Non-limiting examples of essential fatty acids include polyunsaturated fatty acids (PUFAs), fatty acids derived from seafood, fatty acids derived from plants, fatty acids derived from algae, and any combination thereof. As used herein, the term PUFA refers to long chain fatty acids having at least 18 carbons atoms. The PUFA may be an omega-3 fatty acid in which the first double bond occurs in the third carbon-carbon bond from the methyl end of the carbon chain (i.e., opposite the carboxyl acid group). Non-limiting examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may can also be an omega-5 fatty acid, in which the first double bond occurs in the fifth carbon-carbon bond from the methyl end. Exemplary omega-5 fatty acids include myristoleic acid (14:1), myristoleic acid esters, and cetyl myristoleate. The PUFA can also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22:1), and nervonic acid (24:1).

A seafood-derived oil can be derived from a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived include, but are not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

Plant and vegetable oils are rich in omega-6 fatty acids. Some plant-derived oils, such as flaxseed oil, are especially rich in omega-3 fatty acids. Plant or vegetable oils are generally extracted from the seeds of a plant but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, perilla seed oil, pine nut oil, pistachio oil, poppy seed oil, prune kernel oil, pumpkin seed oil, quinoa oil, ramtil oil, rice bran oil, safflower oil, sesame oil, soybean oil, sunflower oil, tea oil, thistle oil, walnut oil, or wheat germ oil. The plant derived oil may also be hydrogenated or partially hydrogenated.

Commercially available algae-derived oils include those from *Crypthecodinium cohnii* and Schizochytrium sp. Other suitable species of algae, from which oil is extracted, include *Aphanizomenon flos-aquae, Bacilliarophy* sp., *Botryococcus braunii, Chlorophyceae* sp., *Dunaliella tertiolecta, Euglena gracilis, Isochrysis galbana, Nannochloropsis salina, Nannochloris* sp., *Neochloris oleoabundans, Phaeodactylum tricornutum, Pleurochrysis carterae, Prymnesium parvum, Scenedesmus dimorphus, Spirulina* sp., and *Tetraselmis chui.* xvii. Amino Acids

The dietary supplement may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include L-histidine, L-isoleucine, L-leucine, L-lysine, L-methionine, L-phenylalanine, L-valine and L-threonine.

xviii. Antioxidants

The dietary supplement can include one or more suitable antioxidants. As will be appreciated by a skilled artisan, the suitability of a given antioxidant will vary depending upon the species to which the dietary supplement will be administered. Non-limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, sodium thiosulfate, or any combination thereof.

Natural antioxidants that may be included in the dietary supplement include, but are not limited to, apple peel extract, blueberry extract, carrot juice powder, clove extract, coffeeberry, coffee bean extract, cranberry extract, eucalyptus extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, turmeric, and wheat germ oil.

(d) Aspects of Powder Compositions

As explained herein above, the present disclosure encompasses gel compositions or powder compositions for preparing the gel compositions, and methods of using the gel compositions to orally administer active ingredients such as delicate vaccines and probiotics to animals, in particular pigs. In some aspects, a composition of the instant disclosure is a powder composition.

In some aspects, the powder composition comprises a gelling agent, a gel activator, a buffering agent, and an electrolyte. The gelling agent can be as described in Section I(a). In some aspects, the gelling agent is agar, alginate, carrageenan, gum Arabic, ghatti, tragacanth, pectin, guar, Gelan, Carboxy Methylcellulose or locust bean gum, or any combination thereof. In some aspects, the gelling agent is alginate.

The gel activator can be as described in Section I(b). In some aspects, the gel activator is dicalcium phosphate, calcium carbonate, calcium gluconate, calcium iodate, calcium oxide, calcium sulfate, or any combination thereof. In some aspects, the buffering agent is phosphates, carbonates, citrates, tris buffers, and buffered saline salts (e.g., Tris buffered saline or phosphate buffered saline), or any combination thereof. For instance, the buffering agent can be disodium phosphate, monopotassium phosphate, and sodium bicarbonate.

The buffering agent can be as described in Section I(c). In some aspects, the buffering agent is a salt of sodium, magnesium, potassium, calcium, chloride, phosphate, bicarbonate, or any combination thereof. In some aspects, the electrolyte is sodium chloride and potassium chloride.

In some aspects, a dry blend of the composition comprises a composition of Table 1.

The active ingredient can be a live vaccine, probiotics, prebiotics, antibody proteins, targeted nutrients, pheromones, pain medication, or any combination thereof. In some aspects, the animal is a pig. When the animal is a pig, the active ingredient can be a vaccine and the vaccine is a *Salmonella* spp. vaccine, an *E. coli* vaccine, an Erysipelas vaccine, a *Lawsonia* (ileitis) vaccine, or any combination thereof.

TABLE 1

| Component | Percent of dry blend, by weight |
|---|---|
| Calcium sulfate (gel activator) | 83.40 |
| Sodium alginate (gelling polymer) | 13.08 |
| Maltodextrin (excipient) | 1.54 |
| FD&C green blend (artificial coloring) | 0.62 |
| Berry flavor (artificial flavoring) | 0.39 |
| Disodium phosphate (pH buffer) | 0.39 |
| Sweetener (artificial flavoring) | 0.23 |
| Sodium chloride (electrolyte) | 0.15 |
| Sodium thiosulfate (reducing agent/antioxidant) | 0.10 |
| Monopotassium phosphate (pH buffer) | 0.06 |
| Potassium chloride (electrolyte) | 0.04 |
| Sodium bicarbonate (pH buffer) | 0.01 |

II. Gel Composition

Another aspect of the instant disclosure encompasses a gel composition for oral administration of an active ingredient to an animal. The composition comprises a dry powder gel composition and water. The dry powder composition can be as described in Section I herein above. In some aspects, the dry powder composition comprises a gelling agent; a gel activator; a buffering agent; and an electrolyte. In some aspects, the dry powder composition comprises a composition of Table 1. When the powder composition comprises a composition of Table 1, the powder composition can be solubilized at a rate of about 12.5% by wt to about 13.5% by wt of the dry powder in one liter of water. In some aspects, the gel composition comprises about 400 to about 125 g to about 135 g of the dry powder in one liter of water.

III. Therapeutic Compositions

Another aspect of the instant disclosure encompasses consumable therapeutic compositions. As explained herein above, the compositions and methods of the disclosure provide means to deliver active ingredients such as the Erysipelas vaccine orally without resorting to traditional methods of administering to animals using dosing tools. Accordingly, compositions of the instant disclosure also encompass vaccine and other therapeutic compositions comprising the powder or gel compositions of the instant disclosure and an active ingredient. The powder compositions can be as described in Section I and the gel compositions can be as described in Section II. The active ingredient can be a vaccine, a pharmaceutical, or a combination thereof. The pharmaceuticals and vaccines can be as described herein below.

(a) Vaccines

One aspect of the instant disclosure encompasses a vaccine composition for vaccinating an animal. In some aspects, the vaccine composition comprises a powder or gel composition and a vaccine. The powder and gel compositions can be as described herein above in Sections I and II herein above, respectively.

A vaccine of the instant disclosure can be any orally administered vaccine (enteric vaccine). Orally administered vaccines for animals are vaccines that are taken through the mouth, either through feed or water. These types of vaccines are commonly used in livestock and poultry farming, as they are convenient and cost-effective.

Vaccines have specific requirements for storage and handling to ensure their stability and effectiveness before administration. Improper storage can result in a loss of vaccine potency or viability, reducing the vaccine's ability to stimulate an immune response and protect against the target disease. Specifically, the vaccine must be kept at the recommended temperature and protected from light and moisture to prevent degradation of the live bacteria. In addition, the vaccine should not be used beyond its expiration date.

It is also important to note that oral vaccines can be subject to some challenges related to their administration. The vaccine may not be evenly distributed in the water or feed, leading to uneven uptake by the animals. Additionally, some animals may not consume enough of the vaccine to achieve full protection. Finally, the vaccine can be impacted by factors such as the animal's gut health, immune status, and age, which can affect its efficacy. Vaccines generally comprise an antigen and an adjuvant.

A. Antigen

Antigens are the component of vaccines that triggers the immune system to recognize and attack a specific pathogen. An antigen is any molecule that can be recognized by the immune system as foreign, such as a protein or carbohydrate on the surface of a virus or bacterium. When an antigen enters the body, the immune system recognizes it as foreign and mounts a response to destroy it. Vaccines use antigens to stimulate the immune system to produce an immune response without causing disease. The antigen in a vaccine can be derived from a live or inactivated pathogen, a piece of the pathogen, or a synthetic version of the pathogen's surface protein. By presenting the immune system with an antigen in a vaccine, the body can produce an immune response and create a memory of how to fight the pathogen if it is encountered again in the future.

Antigens can be, without limitation, polypeptides, proteins, protein fragments, DNA or RNA fragments, hapten-carrier combinations, oligosaccharides or polysaccharides, oligonucleotides or polynucleotides, live attenuated viruses and/or bacteria, other antigenic compounds. or a DNA/RNA sequence coding for any of the above. For example, these may be derived from pathogenic organisms such as viruses, bacteria, parasites, or the like, and may optionally comprise a fragment of an antigen originating from these organisms, or they can be prepared synthetically and correspond to natural antigenic determinants or may be derived from these.

The antigen component(s) can include a component active against one or more disease pathogens, for example, any pathogenic, bacterial, viral (DNA or RNA), protozoan, mycoplasma, or parasitic disease. For example, the disease pathogen can be selected from the group consisting of, but not limited to Adenovirus, AIDS, Anthrax, BCG, Chlamydia, Cholera, Circovirus, Classical swine fever, Coronavirus, Diphtheria-Tetanus (DT for children), Diphtheria-Tetanus (tD for adults), Distemper virus, DTaP, DTP, *E. coli*, Eimeria (coccidiosis), Encephalitis, Feline immunodeficiency virus, Feline leukemia virus, Foot and mouth disease, Hemophilus, Hepatitis A, B, C, D, E, F, Hepatitis B/Hib, Herpes virus, Hib, Influenza, Japanese Encephalitis, Lyme disease, Measles, Measles-Rubella, Meningococcal, MMR, Mumps, Mycoplasma, Para influenza virus, Parvovirus, Pasteurella, Pertussis, Pestivirus, Plague, Pneumococcal, Polio (IPV), Polio (OPV), circovirus, parvovirus, Pseudorabies, Rabies, Respiratory syncytial virus, Rhinotracheitis, Rotavirus, Rubella, *Salmonella*, SARS, Tetanus, Typhoid, Varicella, Viral diarrhea virus, and Yellow fever. Other examples of orally administered vaccines for animals include the oral avian influenza vaccine for poultry, oral myxomatosis vaccine for rabbits, and oral typhoid vaccine for chickens.

In some aspects, the vaccine is an orally administered vaccine administered to an animal. Orally administered vaccines for animals are commonly used to protect against various infectious diseases. Some examples include the oral rabies vaccine for wild animals, oral *Salmonella* and *E. coli* vaccines for poultry and livestock, and oral rotavirus vaccines for calves and pigs. Other vaccines include the oral infectious bronchitis vaccine and the oral avian encephalomyelitis vaccine for poultry, the oral infectious hematopoietic necrosis vaccine for fish, and the oral *staphylococcus* vaccine for pigs. Additionally, there are oral vaccines available for preventing erysipelas in pigs, as well as transmissible enteritis and Gumboro disease in chickens.

In some aspects, the oral vaccine prevents or controls Erysipelothrix rhusiopathiae infection (Erysipelas). Erysipelas has a worldwide distribution and is of economic importance throughout Europe, Asia, Australia and North and South America. Pigs 3 months through 3 years of age are most susceptible to erysipelas. Affected pigs often have fever, skin lesions, swollen and stiff joints and they do not gain weight efficiently. Also, their carcasses are often trimmed or condemned by inspectors at packing houses. The oral vaccine for erysipelas can be made from live attenuated bacteria and can be given to pigs via drinking water or feed. It can provide long-lasting protection against the disease and is commonly used in pig herds to prevent outbreaks.

In some aspects, the oral vaccine is a vaccine against *Salmonella* sp. Orally administered *Salmonella* vaccines are commonly used in the agriculture industry to prevent and control the spread of *Salmonella* infections in animals. Poultry, in particular, are often vaccinated with oral *Salmonella* vaccines through drinking water or feed. These vaccines can provide long-lasting protection against several strains of *Salmonella*, which can cause serious health issues in both animals and humans. The vaccines work by inducing an immune response in the animal's gut, which helps prevent *Salmonella* colonization and shedding. In addition to vaccination, proper hygiene and sanitation practices are also crucial in preventing *Salmonella* infections. It is important to consult with a veterinarian to determine the best vaccination strategy for individual animals and flocks.

In some aspects, the oral vaccine is a *Lawsonia* (ileitis) vaccine. *Lawsonia* intracellularis, commonly known as ileitis, is a bacterial disease that affects the intestines of pigs, causing chronic diarrhea, weight loss, reduced growth rates, and death from the acute form of the disease (acute porcine proliferative enteropathy (PPE)). The disease can have significant economic consequences for pig producers. The vaccine can comprise live attenuated bacteria that stimulate an immune response in the pig's gut, leading to the production of protective antibodies against *Lawsonia* intracellularis. The oral vaccine can be administered via the drinking water, making it a convenient and effective option for large-scale pig production. Vaccination can reduce the incidence and severity of ileitis, leading to improved growth rates and overall health in the pig population. However, it is important to note that vaccines alone may not be enough to prevent the disease entirely, and other measures such as biosecurity and proper sanitation practices should also be implemented to control the spread of ileitis. Veterinarians can provide guidance on the best vaccination protocols and management practices to help prevent and control the disease.

In some aspects, the oral vaccine is to prevent or control *E. coli*. *E. coli*, or *Escherichia coli*, is a common bacterial species that can cause disease in both humans and animals. In animals, *E. coli* infections can lead to a range of diseases, including diarrhea, septicemia, urinary tract infections, and acute death caused by some strains such as F18/K88. One method of controlling *E. coli* infections in animals is through the use of oral vaccines. Oral *E. coli* vaccines for animals contain live attenuated bacteria that have been modified to stimulate an immune response without causing disease. When administered orally, the vaccine bacteria colonize the animal's gut, triggering the production of antibodies and other immune system components that can protect against infection by virulent *E. coli* strains. Oral *E. coli* vaccines have been shown to be effective in controlling *E. coli* infections in a variety of animal species, including pigs, cattle, and poultry. In pigs, for example, oral vaccination has been shown to reduce the incidence and severity of post-weaning diarrhea, a common problem that can result in significant economic losses for pig producers. Similarly, in poultry, oral vaccination has been used to control *E. coli* infections that can lead to respiratory disease, septicemia, and other health issues. However, like all vaccines, oral *E. coli* vaccines have specific requirements for storage, handling, and administration to ensure their effectiveness. The vaccines must be kept at the recommended temperature and protected from light and moisture to prevent degradation of the live bacteria. In addition, the vaccines should be administered at the appropriate time and in the recommended dosage to ensure adequate protection.

In some aspects, the oral vaccine is to prevent or control *Clostridium*. *Clostridium* is a genus of bacteria that includes several species that can cause serious and often fatal diseases in animals, such as cattle, sheep, and goats. These diseases include blackleg, tetanus, botulism, and enterotoxemia, which can cause significant economic losses for livestock producers. One method of controlling these diseases is through the use of oral vaccines. Oral clostridial vaccines for animals contain inactivated or attenuated bacteria that stimulate the production of antibodies in the animal's immune system. When administered orally, the vaccine bacteria colonize the animal's gut and stimulate an immune response that can protect against virulent strains of *Clostridium*. The vaccines are typically given to young animals, as they are more susceptible to these diseases. Oral clostridial vaccines have been shown to be effective in controlling clostridial diseases in a variety of animal species, including cattle, sheep, and goats. For example, vaccination against blackleg has been shown to reduce the incidence of disease in cattle and sheep, while vaccination against enterotoxemia has been shown to reduce the incidence of disease in sheep and goats. Like all vaccines, oral clostridial vaccines have specific requirements for storage, handling, and administration to ensure their effectiveness. The vaccines must be kept at the recommended temperature and protected from light and moisture to prevent degradation of the bacteria. In addition, the vaccines should be administered at the appropriate time and in the recommended dosage to ensure adequate protection.

In some aspects, the oral vaccine is to prevent or control coronaviruses. Coronaviruses are a group of RNA viruses that cause respiratory and enteric diseases in various animal species. In animals, coronaviruses can cause diseases such as feline infectious peritonitis (FIP) in cats, porcine epidemic diarrhea (PED) in pigs, and infectious bronchitis (IB) in chickens. These diseases can result in significant economic losses for farmers and the livestock industry. Oral vaccines against coronaviruses have been developed for some animal species, including chickens and pigs. These vaccines can help prevent the spread of the disease by inducing immunity in animals before exposure to the virus. However, as with any vaccine, proper storage and handling are crucial to maintaining vaccine efficacy.

In some aspects, the oral vaccine is to prevent or control *Brachyspira*. *Brachyspira* is a genus of bacteria that can cause intestinal diseases in various animal species, including pigs and poultry. These diseases can lead to reduced growth rates, poor feed conversion, and diarrhea, resulting in significant economic losses for farmers and the livestock industry. Oral vaccines against *Brachyspira* have been developed for use in pigs, which can help protect animals against diseases such as swine dysentery and porcine intestinal spirochetosis. These vaccines contain live, attenuated bacteria that can stimulate an immune response in pigs and induce protective immunity against future infections. Proper storage and handling of these vaccines are crucial to maintain vaccine efficacy, and vaccination alone may not be sufficient to prevent disease outbreaks. Therefore, it is important for farmers to implement appropriate biosecurity measures and good management practices to reduce the risk of *Brachyspira* infections in their animals.

B. Adjuvant

As stated above, the vaccine composition further includes a pharmaceutically acceptable, preferably non-liquid, adjuvant. The adjuvant can be of any suitable type. As used herein, the term "adjuvant" refers to any substance that enhances the immune response against the targeted pathogen or antigen.

There are different types of adjuvants, including without limitation. (1) Alum: This is the most commonly used adjuvant in human vaccines. It consists of aluminum salts, which can enhance the immune response to the vaccine antigen. (2) Oil-in-water emulsions: These adjuvants are used in some human and veterinary vaccines. They consist of oil droplets suspended in a water-based solution, which can enhance the immune response by providing a slow release of the antigen. (3) Liposomes: These adjuvants are made of lipids and can deliver antigens directly to antigen-presenting cells, which can improve the immune response. (4) Virosomes: These adjuvants are derived from viruses and can enhance the immune response by mimicking the natural infection process. (5) Cytokines: These are naturally occurring proteins that can enhance the immune response by stimulating the production of immune cells and enhancing their function. (6) Toll-like receptor agonists: These adjuvants can activate the immune system by stimulating the production of cytokines and other immune molecules.

Non-limiting examples of salts suitable for a composition of the instant disclosure include mineral salts, saponins such as Quil A, mineral oils such as Marcol 52 non-mineral oils, such as Montanide 103 (SEPPIC, Paris, and pluronic polymers, such as L121 (BASF, N.J.), squalene and squalene, Adjuvant 65 (containing peanut oil, mannide monooleate and aluminium monostearate), surfactants such as hexadecylamine, octadecylamine, lysolecithin, dimethyl-dioctadecylammonium bromide, N,N-dioctradecyl-N,N1-bis(2-hydroxyethyl)-propanediamine, methoxy-hexadecylglycerol and pluronic polyols, polyanions such as pyran, dextran sulfate, polyacrylic acid and carbopol, peptides and amino acids such as muramyl dipeptide, demethylglycine, tuftsin and trehalose dimycolate, Adju-Phos, Algal Glucan, Algammulin, aluminium salts including aluminium hydroxide (Al(OH)3), aluminium phosphate (AlPO4), Alhydrogel, Antigen Formulation, Avridine, Bay R1005, Calcitriol, Calcium Phosphate, Calcium Phosphate Gel, Cholera Holotoxin (CT), Cholera Toxin B Subunit (CTB), CRL1005, DDA, DHEA, DMPC, DMPG, DOC/Alum Complex, Gamma Inulin, Gerbu Adjuvant, GMDP, Imiquimod, ImmTher, Interferon-gamma, Iscoprep 7.0.3, Loxoribine, LT-OA or LT Oral Adjuvant, MF59, Mannan, MONTANIDE ISA 51, MONTANIDE ISA 720, MPL, MTP-PE, MTP-PE, Murametide, Murapalmitine, D-Murapalmitine, NAGO, Nonionic Surfactant Vesicles, Pleuran, PLGA, PGA and PLA, Pluronic L121, PMMA, PODDS, Poly Ra: Poly rU, Polyphosphazene, Polysorbate 80, Protein Cochleates, QS-21, Quil A, Rehydragel HPA, Rehydragel LV, S-28463, SAF-1, Sclavo Peptide, Sendai Proteoliposomes, Sendai-Containing Lipid Matrices, Span 85, Specol, Stearyl Tyrosine, Theramide, Threonyl-MDP, Ty Particles, or any combination thereof.

C. Vaccine Composition

One aspect of the instant disclosure encompasses a vaccine composition for vaccinating an animal. In some aspects, the vaccine composition comprises a gel composition and a vaccine. The gel composition can be as described in Section II and the vaccine can be as described in Section III(a) herein above. In some aspects, the animal is a pig. When the animal is a pig, the vaccine can be a *Salmonella* spp. vaccine, an *E. coli* vaccine, an Erysipelas vaccine, a *Lawsonia* (ileitis) vaccine, or any combination thereof. In some aspects, the vaccine is an Erysipelas vaccine. In some aspects, the vaccine is a hemolytic *E. coli* vaccine.

(b) Pharmaceuticals

Another aspect of the instant disclosure encompasses a pharmaceutical composition for administration of an active ingredient to an animal. In some aspects, the pharmaceutical composition comprises a powder or gel composition and a pharmaceutical. The powder and gel compositions can be as described herein above in Sections I and II herein above, respectively.

Any pharmaceutical suitable for administration to an animal can be used in a pharmaceutical composition of the instant disclosure. For instance, non-limiting examples of a suitable pharmaceutical that can be used in a composition of the instant disclosure include a low molecular weight active ingredient, a probiotic, a prebiotic, a semiochemical, or any combination thereof. Other pharmaceuticals suitable for a therapeutic composition of the instant disclosure can be apparent to an individual of skill in the art. The powder and gel compositions can be as described herein above in Section I.

A. Low Molecular Weight Active Ingredients

In some aspects, the active ingredient is a low molecular weight active ingredient. Accordingly, another aspect of the instant disclosure encompasses a therapeutic composition for administering a low molecular weight active ingredient to an animal. In some aspects, the probiotic composition comprises a powder or gel composition and a low molecular weight active ingredient. The powder and gel compositions can be as described herein above in Sections I and II herein above, respectively.

Pharmaceuticals that can be included in compositions of the instant disclosure can be low-molecular-weight drugs such as antibiotics, anti-inflammatory drugs, alkylating agents, immunosuppressants, or any combination thereof.

Non-limiting examples of oral pharmaceuticals for animals include antibiotics; antifungals; nonsteroidal anti-inflammatory drugs (NSAIDs) and other anti-inflammatories; anthelmintics; antiparasitics such as coccidiostats; antihistamines; antidepressants; chemotherapy drugs; heart medications; pain medications; or any combination thereof.

In some aspects, the drug can be an antibiotic. Non-limiting examples of antibiotics include Amikacin, Gentamicin, Kanamycin, Neomycin, Netilmicin, Tobramycin, Paromomycin, Geldanamycin, Herbimycin, Carbacephem, Loracarbef, Ertapenem, Doripenem, Imipenem/Cilastatin, Meropenem, Cefadroxil, Cefazolin, Cefalotin, Cefalexin, Cephalosporins, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole (such as Bactrim, Septra), Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, Tinidazole.

In some aspects, the pharmaceutical is an antifungal. Non-limiting examples of antifugal drugs include Acrisorcin; Ambruticin; Azaconazole; Azaserine; Basifungin; Bifonazole; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Itraconazole; Kalafungin; Ketoconazole; Lomoftmgin; Lydimycin; Mepartricin; Miconazole; Miconazole Nitrate; Monensin; Monensin Sodium; Naftifine Hydrochloride; Nifuratel Nifurmerone; Nitralamine Hydrochloride; Nystatin; Octanoic Acid; Orconazole Nitrate; Oxiconazole Nitrate; Oxifingin Hydrochloride; Parconazole Hydrochloride; Partricin; Potassium Iodide; Pyrrolnitrin; Rutamycin; Sanguinarium Chloride; Saperconazole; Selenium Sulfide; Sinefingin; Sulconazole Nitrate; Terbinafine; Terconazole; Thiram; Tioconazole; Tolciclate; Tolindate; Tolnaftate; Triacetin; Triafungin; Undecylenic Acid; Viridofulvin; Zinc Undecylenate; Zinoconazole Hydrochloride.

In some aspects, the pharmaceutical is a non-steroidal active ingredient (NSAIDs). Non-limiting examples of NSAIDs include acetylsalicylic acid or sodium salicyclic; meloxicam; Alclofenac; Amfenac Sodium; Apazone; Carprofen; Cicloprofen; Cintazone; Cliprofen; Clopirac; Diclofenac Potassium; Diclofenac Sodium; Etodolac; Fenbufen; Fenclofenac; Fentiazac; Flufenamic Acid; Fluretofen; Ibuprofen; Ibuprofen Aluminum; Ibuprofen Piconol; Indomethacin Sodium; Indomethacin; Indoprofen Indoxole; Isoxicam; Ketoprofen; Lomoxicam; Meclofenamate Sodium; Meclofenamic Acid; Morniflumate; Nabumetone; Oxyphenbutazone; Phenylbutazone; Robenacoxib; Sodium Glycerate; Piroxicam; Piroxicam Cinnamate; Pirprofen; Salnacedin; Sulindac; Suprofen; Tenidap; Tenidap Sodium; Tenoxicam; Tolmetin; Tolmetin Sodium; or any combination thereof.

Other anti-inflammatories include Algestone Acetonide; Alpha Amylase; Amcinafal; Amcinafide; Anakinra; Anitrazafen; Apazone; Balsalazide Disodium; Bendazac; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diflorasone Diacetate; Diflumidone Sodium; Difluprednate; Diftalone; Dimethyl Sulfoxide; Drocinonide; Endrysone; Enlimomab; Enolicam Sodium; Etodolac; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Fluocortin Butyl; Fluorometholone Acetate; Fluquazone; Fluretofen; Fluticasone Propionate; Furaprofen; Furobufen; Halcinonide; Halobetasol Propionate; Halopredone Acetate; Ilonidap; indomethacin Sodium; Indomethacin; Indoprofen Indoxole; Intrazole; Isoflupredone Acetate; Isoxepac; Isoxicam; Lomoxicam; Loteprednol Etabonate; Meclofenamate Sodium; Meclofenamic Acid; Meclorisone Dibutyrate; Mesalamine; Meseclazone; Methylprednisolone Suleptanate; Morniflumate; Nabumetone; Nimazone; Olsalazine Sodium; Orgotein; Orpanoxin; Oxaprozin; Oxyphenbutazone; Paranyline Hydrochloride; Pentosan Polysulfate Sodium; Phenylbutazone Sodium Glycerate; Piroxicam; Piroxicam Cinnamate; Pirprofen; Prednazate; Prednisolone Sodium Phosphate; Prifelone; Prodolic Acid; Proquazone; Rimexolone; Romazarit; Salnacedin; Seclazone; Sermetacin; Sudoxicam; Sulindac; Suprofen; Talniflumate; Tenidap; Tenidap Sodium; Tenoxicam; Tesicam; Tesimide; Tixocortol Pivalate; Tolmetin; Tolmetin Sodium; Triclonide; Triflumidate; Zidometacin.

Non-limiting examples of antiparasitics include Albendazole, Ivermectin, Mebendazole, Nitazoxanide, Pyrantel Pamoate, Chloroquine, Quinine, Artemether/Lumefantrine, Atovaquone/Proguanil, Mefloquine, Primaquine, Metronidazole, Tinidazole, Pentamidine, Suramin, Melarsoprol, Eflornithine, Nifurtimox, Benznidazole, Diethylcarbamazine.

Non-limiting examples of antihistaminics include Acrivastine; Antazoline Phosphate; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cirmarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Fexofenadine HCl; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; Triprolidine Hydrochloride.

In some aspects, a pharmaceutical can be a coccidiostat. Coccidiostats are a group of drugs that are used to prevent or treat infections caused by protozoan parasites called coccidia. Coccidia are commonly found in animals, particularly in poultry, cattle, and pigs, and can cause a range of health problems, including diarrhea, weight loss, decreased productivity, and in severe cases, death. Coccidiostats work by interfering with the life cycle of the coccidia, either by preventing the parasites from reproducing or by killing them outright. There are several different types of coccidiostats, each with a slightly different mechanism of action. Non-limiting examples of coccidiostats include Amprolium; Decoquinate; Diclazuril; Monensin; Toltrazuril; Arprinocid; Narasin; Semduramicin; Semduramicin Sodium; Ponazuril; essential oils for coccidia, or any combination thereof. Non-limiting examples of essential oils suitable for use as a coccidiostat include mentha species oils, garlic oils, and capsicum oleoresins.

In some aspects, the drug can be an anthelminthic. Non-limiting examples of anthelminthics include Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; piperazine; piperazine Citrate; piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Praziquantal; Triclofenol piperazine; Vincofos; Zilantel; Albendazole; Fenbendazole; Ivermectin; Mebendazole; Pyrantel pamoate; Levamisole; Praziquantel; Niclosamide; Diethylcarbamazine; Piperazine; Thiabendazole; Oxfendazole; Triclabendazole; and Febantel.

In one aspect, the drug can be a pain medication. Non-limiting examples of pain medication include meloxicam; Propionic acid derivatives (ibuprofen, naproxen, ketoprofen, flurbiprofen, indomethacin, diclofenac, ketolorac), Enolic acid derivatives (Piroxicam, meloxicam, tenoxicam, droxicam, lornoxicam, phenylbutazone), Flunixin, Anthranilic acid derivatives (tolfenamic acid, flufenamic acid, meclofenamic acid, mefenamic acid) Coxibs (celecoxib, parecoxib, firocoxib, and etoricoxib.

B. Probiotics

Yet another aspect of the instant disclosure encompasses a gel probiotic composition for administering a live probiotic, a prebiotic, or a combination thereof (herein referred to collectively as probiotics) to an animal. In some aspects, the probiotic composition comprises a powder or gel composition and a probiotic. The powder and gel compositions can be as described herein above in Sections I and II herein above, respectively.

In some aspects, the probiotic of the instant disclosure is a live probiotic. Live probiotics are live microorganisms that, when administered in adequate amounts, confer a health benefit to the host. These microorganisms include bacteria, yeast, and other microorganisms that are commonly found in the gut of animals, including humans. Probiotics work by restoring the balance of good and bad bacteria in the gut, which can be disrupted by factors such as stress, illness, and the use of antibiotics. Probiotics are commonly used as a dietary supplement for humans, and they are also used in animal feed to promote gut health and improve animal performance. Probiotics and prebiotics can include yeast and bacteria that help establish an immune protective rumen or gut microflora as well as small oligosaccharides. There are many different types of probiotics that are commonly used for animals. Non-limiting examples of probiotics for animals include *Lactobacillus acidophilus, Bifidobacterium bifidum, Streptococcus thermophilus, Saccharomyces cerevisiae, Bacillus subtilis, Enterococcus faecium*, and strains derived therefrom.

In some aspects, the probiotic of the instant disclosure is a prebiotic. Prebiotics can include yeast-derived and bacteria-derived prebiotics. By way of non-limiting examples, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei, Aspergillus oryzae*, or any combination thereof.

Prebiotics can also include bacteria cell wall derived agents such as peptidoglycan and other components derived from gram-positive bacteria with a high content of peptidoglycan. Non-limiting exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii, Bifidobacterium pseudolongum*, or any combination thereof.

Non-limiting examples of other prebiotics include resistant starch. Resistant starch refers to starch, plus its digestion products that are not absorbed in the small intestine and pass to the large bowel and beneficially modify gut microbial populations. Resistant starch can be categorized into (a) physically inaccessible starches (RS1), (b) resistant granules (RS2), (c) retrograde starch (RS3), and (d) chemically modified starch (RS4). It can be found in foods like unripe bananas, cooked and cooled potatoes, and legumes. Non-limiting examples of resistant starch include cornstarch, green banana flour, cassava starch, wheat dextrin, oat bran, barley, chicory root fiber, konjac glucomannan, and any combination thereof. In some aspects, a gel or powder composition of the instant disclosure comprises potato starch (RS2).

C. Semiochemicals

An additional aspect of the instant disclosure encompasses a gel or powder composition comprising a semiochemical for administering the semiochemical to an animal. In some aspects, the semiochemical composition comprises a powder or gel composition and a semiochemical. The powder and gel compositions can be as described herein above in Sections I and II herein above, respectively.

A semiochemical is a chemical substance or mixture of substances released by an organism that affects the behaviors of other individuals. Semiochemical communication can be divided into two broad classes: communication between individuals of the same species (intraspecific) or communication between different species (interspecific). Semiochemicals encompass pheromones, allomones, kairomones, synomone, attractants and repellents. Some semiochemicals can function as any combination of a pheromone, allomone, kairomone, attractant and repellent.

In some aspects, the semiochemical is an allomone. An allomone is any chemical substance released by an individual of one species that affects the behavior of a member of another species to the benefit of the originator but not the receiver. Production of allomones is a common form of defense, such as by plant species against insect herbivores or prey species against predators. Sometimes, species produce the sex pheromones of the organisms they exploit as prey or pollinators (such as bolas spiders and some orchids).

In some aspects, the semiochemical is a kairomone. A kairomone is a semiochemical, emitted by an organism, which mediates interspecific interactions in a way that benefits an individual of another species which receives it, without benefitting the emitter. Two main ecological cues are provided by kairomones; they generally either indicate a food source for the receiver or give warning of the presence of a predator. Often a pheromone can be utilized as a kairomone by a predator or parasitoid to locate the emitting organism.

In some aspects, the semiochemical is a synomone. A synomone is an interspecific semiochemical that is beneficial to both interacting organisms, the emitter and receiver, e.g. floral synomone of certain Bulbophyllum species (Orchidaceae) attracts fruit fly males (Tephritidae: Diptera) as pollinators. In this true mutualistic inter-relationship, both organisms gain benefits in their respective sexual reproductive systems—i.e. orchid flowers are pollinated and the Dacini fruit fly males are rewarded with a sex pheromone precursor or booster. The floral synomone, also acts as a reward to pollinators, is either in the form of a phenylpropanoid (e.g. methyl eugenol) or a phenylbutanoid (e.g. raspberry keton and zingerone).

In some aspects, the semiochemical of the instant disclosure is a behavior-modifying pheromone. A pheromone is a secreted or excreted chemical factor that triggers a social response in animals. Pheromones are chemicals capable of acting like hormones outside the body of the secreting individual, to affect the behavior of the receiving individuals. There are alarm pheromones, food trail pheromones, sex pheromones, behavior-modifying pheromones and many others that affect behavior or physiology. Pheromones are used by many organisms, from basic unicellular prokaryotes to complex multicellular eukaryotes.

Behavior-modifying semiochemicals can be categorized by function, such as aggregation semiochemicals, alarm semiochemicals, epideictic semiochemicals, territorial semiochemicals, trail semiochemicals, sex semiochemicals, territorial semiochemicals, territorial semiochemicals, calming (appeasing) semiochemicals, and suckling semiochemicals among others. The semiochemical can be a releaser semiochemical, a primer semiochemical, and a signal semiochemical among others. Releaser semiochemicals are semiochemicals that cause an alteration in the behavior of the recipient. For example, some organisms use powerful attractant molecules to attract mates from a distance. In general, this type of semiochemical elicits a rapid response, but is quickly degraded. For example, rabbit mothers release mammary semiochemicals that trigger immediate nursing behavior by their babies. A primer pheromone has a slower onset and a longer duration. Primer pheromones trigger a change of developmental events (in which they differ from all the other pheromones, which trigger a change in behavior). Signal pheromones cause short-term changes, such as the neurotransmitter release that activates a response. For instance, GnRH molecule functions as a neurotransmitter in rats to elicit lordosis behavior.

Pig pheromones are chemicals produced by pigs that play a role in communication and social behavior. These chemicals can be used for a variety of purposes, including attracting mates, marking territories, and signaling social status. Here are some of the pheromones produced by pigs: Androstenone: This is a male pheromone that is found in high concentrations in the saliva and sweat of male pigs. It is known to induce sexual arousal in female pigs and is used to detect sexual maturity in male pigs. Androstenol: This is a pheromone produced by both male and female pigs. It is believed to have a calming effect on other pigs and can be used to reduce aggression in males. Estratetraenol: This is a female pheromone that is produced in the urine of female pigs. It is used to attract male pigs during the breeding season. Skatole: This is a pheromone that is produced in the feces of pigs. It is believed to play a role in territorial marking and may be used to signal dominance. Copulins: These are female pheromones that are produced in the vaginal secretions of female pigs. They are used to attract males during the breeding season. Boar taint pheromones: These are a group of pheromones produced by male pigs that are responsible for the unpleasant odor associated with boar meat. They include androstenone, skatole, and indole. Z3-hexenol: This is a pheromone produced by pigs in response to stress. It is believed to have a calming effect on other pigs and can be used to reduce aggression. 3-methylindole: This is a pheromone produced in the feces of pigs. It is believed to play a role in territorial marking and may be used to signal dominance. Indole: This is a pheromone produced in the feces of pigs. It is believed to play a role in territorial marking and may be used to signal dominance. 3-methylbutanol: This is a pheromone produced in the saliva of pigs. It is believed to play a role in social bonding and can be used to reduce aggression.

In certain aspects, maternal semiochemicals that attract piglets. Non-limiting examples of maternal semiochemicals include 3-methylbutanoic acid, pentanoic acid, 4-methylphenol, methyl 13-methyltetradecanoate, methyl 12-methyltetradecanoate, methyl pentadecanoate, methyl 14-methylpentadecanoate, methyl hexadecanoate, methyl 14-Methyl Hexadecanoate, methyl 15-methyl Hexadecanoate, methyl heptadecanoate, 1H-Indole, hexadecan-1-ol, 3-methylindole (skatole), methyl octadecanoate, methyl (Z)-octadec-9-enoate, 13-Octadecanoic acid, methyl ester, methyl octadeca-9,12-dienoate, methyl (9Z,12Z,15Z)-octadeca-9,12,15-trienoate, methyl (Z)-heptadec-10-enoate, tetradecanoic acid (myristic acid), 1,3-dihydroindol-2-one, pentadecanoic acid, hexadecanoic acid, skatole, methyl octadeca-9,12-dienoate, and myristic acid. In one aspect, the maternal semichemical is selected from the group consisting of katole and myristic acid.

In some aspects, the semiochemical is a reproductive progestin. Progestins are synthetic or naturally occurring compounds that mimic the effects of the hormone progesterone in the body. Progesterone is a naturally produced hormone in both humans and animals that plays a vital role in the female reproductive system. Progestins are widely used in reproductive medicine and veterinary practice for various purposes, including contraception, hormone replacement therapy, and reproductive management in animals. They exert their effects by binding to progesterone receptors in target tissues, modulating gene expression and influencing physiological processes. In contraception, progestins are commonly used as a component of hormonal contraceptives, such as birth control pills, hormonal patches, intrauterine devices (IUDs), and contraceptive implants. They work by inhibiting ovulation, thickening cervical mucus to impede sperm penetration, and altering the lining of the uterus to prevent implantation. Progestins are also employed in hormone replacement therapy (HRT) for menopausal women. They help alleviate symptoms of menopause, such as hot flashes, vaginal dryness, and mood swings, by supplementing declining levels of progesterone. In veterinary medicine, progestins are utilized to manipulate and control reproductive cycles in animals. They can be used to synchronize estrus (heat) cycles, induce or regulate ovulation, suppress estrus in female animals, and maintain pregnancies. The specific progestin compound, dosage, and administration route can vary depending on the intended use and species being treated. It is crucial to consult with healthcare professionals or veterinarians for proper guidance and prescription when considering the use of reproductive progestins.

D. Aspects of Therapeutic Compositions

One aspect of the instant disclosure encompasses a gel therapeutic composition for oral administration of an active ingredient to an animal. The composition comprises a gel composition and an active ingredient. The gel composition can be as described in Section II and the active ingredient can be as described in Sections III(b)(A-C) herein above.

In some aspects, the active ingredient is a small molecular weight active ingredient. The low molecular weight active ingredient can be as described in Section III(b)(A) herein above. In some aspects, the animal is a pig. In some aspects, the low molecular weight active ingredient is toltrazuril.

In some aspects, the active ingredient is a probiotic. The probiotic can be as described in Section III(b)(B) herein above. In some aspects, the animal is a pig. In some aspects, the active ingredient is a probiotic. The probiotic can be a *Lactobacillus* strain.

IV. Methods

The instant disclosure encompasses methods of preparing gel or powder compositions, vaccine compositions, and therapeutic gel compositions, and methods of using the gel or powder compositions for administering an active ingredient to an animal and methods of treating the animal. The methods are described further herein below.

(a) Animals

Suitable animals include all mammals, avian species, and aquaculture animals. The animal can be a food animal, a companion animal, or a research animal. Non-limiting examples of food animals include poultry (e.g., chickens, including broilers, layers, and breeders, ducks, game hens, geese, guinea fowl/hens, quail, and turkeys), beef cattle, dairy cattle, veal, pigs, goats, sheep, bison, and aquatic animals. Non-limiting examples of suitable companion animals include, but are not limited to, cats, dogs, horses, rabbits, rodents (e.g., mice, rats, hamsters, gerbils, and guinea pigs), hedgehogs, and ferrets. Non-limiting examples of aquatic animals include crustaceans, fishes, shells, mollusks, and amphibians. Non-limiting examples of suitable cultivated aquatic animals include salmon, shrimp, tilapia, catfish, trout, burramundi, crawfish. Non-limiting examples of research animals include rodents, cats, dogs, rabbits, pigs, and non-human primates. Non-limiting examples of suitable zoo animals include non-human primates, lions, tigers, bears, elephants, giraffes, and the like. In some aspects, the animal is a pig.

(b) Animal Diseases

Methods of the instant disclosure can be used to treat a number of animal diseases. Animal diseases in farm animals can have devastating consequences on the agricultural industry and the economy as a whole. Accordingly, effective disease prevention and control measures are critical to minimizing the impact of animal diseases on the agricultural industry and ensuring the health and welfare of farm animals. These diseases can be caused by a variety of pathogens, including without limitation, viruses, bacteria, fungi, parasites, protozoa, helminths, nutritional deficiencies, and prions. An animal disease can also be any disease of unknown cause that can affect an animal's health. For instance, an animal disease can be off feed sows.

Non-limiting examples of viral diseases include foot-and-mouth disease, avian influenza, porcine reproductive and respiratory syndrome, bovine viral diarrhea, rotaviral enteritis, and African swine fever. Viral diseases can rapidly spread and cause significant economic losses due to the need to cull infected animals and the restrictions placed on the movement of livestock.

Non-limiting examples of bacterial diseases include tuberculosis, brucellosis, *salmonellosis*, hemolytic *E. coli*, mastitis, ileitis, Erysipelas, and anthrax. Some bacterial diseases of farm animals can also pose a risk to human health.

Non-limiting examples of parasitic diseases include coccidiosis, cryptosporidiosis, giardiasis, liver fluke, and mange. Parasitic diseases can cause significant production losses and affect the welfare of animals.

Non-limiting examples of fungal diseases include ringworm, aspergillosis, candidiasis, and histoplasmosis which can also affect farm animals and have public health implications.

Prion diseases are caused by abnormal proteins called prions and can affect both animals and humans. Non-limiting examples of prion diseases include bovine spongiform encephalopathy (BSE or "mad cow disease"), scrapie, and chronic wasting disease.

Protozoal diseases are caused by single-celled organisms called protozoa and can affect a variety of farm animals. Non-limiting examples of protozoal diseases include babesiosis, theileriosis, and trypanosomiasis.

In some aspects, an animal disease of the instant disclosure comprises Ileitis, *Salmonella, E coli, Clostridium*, Coronaviruses (PED, TGE, Delta Corona), *Brachyspira*, Rotavirus, erysipelas, *Staphylococcus*, sapovirus, Ascariasis, astrovirus, *Streptococcus suis*, coccidiosis, infectious bronchitis, iron deficiency, off feed animals including sows, or any combination thereof.

(c) Method of Preparing a Gel Composition

Yet another aspect of the instant disclosure encompasses a method for preparing a gel composition for oral administration to an animal. The method comprises solubilizing an amount of a dry powder composition in a volume of water to form a gelling solution; and allowing a sufficient amount period of time for the gelling solution to form a gel. The powder composition can be as described in Section I herein above.

In various aspects, solubilizing an amount of the dry powder composition in a volume of water to form a gelling solution comprises adding about 50 g to about 200 g of the dry powder in one liter of water. In one aspect, about 50 g, about 55 g, about 60 g, about 65 g, about 70 g, about 75 g, about 80 g, about 85 g, about 90 g, about 95 g, about 100 g, about 105 g, about 110 g, about 115 g, about 120 g, about 125 g, about 130 g, about 135 g, about 140 g, about 145 g, about 150 g, about 155 g, about 160 g, about 165 g, about 170 g, about 175 g, about 180 g, about 185 g, about 190 g, or about 200 g in one liter of water. In certain aspect, about 125 g to about 135 g of the dry powder is added to one liter of water.

In another aspect, the gelling solution comprises about 1% (w/v) to about 50% (w/v) of dry powder composition. For example, the gelling solution can comprise about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), or about 50% (w/v). In one aspect, the gelling solution comprises about 10% (w/v) to about 15% (w/v) dry powder composition. In a specific aspect, the gelling solution comprises about 12% (w/v) dry powder composition. In an alternate aspect, the gelling solution comprises about 13% (w/v) dry powder composition.

The water used for preparing the gelling solution may be water that is readily available in the farm, or that is regularly used as a drinking water for the livestock. In one aspect, water is cold water. For example, the water can be about 15° C., about 16° C., about 17° C., about 18° C., about 19° C., about 20° C., about 21° C., about 22° C., about 23° C., about 24° C., or about 25° C.

In further aspects, a period of time for the gelling solution to form a gel may be about 10 minutes to about 30 minutes, 5 minutes to about 20 minutes, or about 1 minute to about 10 minutes. The period of time for gelling solution to form a gel can be about 1 minute, about 2 minutes, about 3 minutes, about 4 minutes, about 5 minutes, about 6 minutes, about 7 minutes, about 8 minutes, about 9 minutes, about 10 minutes, 11 minutes, about 12 minutes, about 13 minutes, about 14 minutes, about 15 minutes, about 16 minutes, about 17 minutes, about 18 minutes, about 19 minutes, about 20 minutes, 21 minutes, about 22 minutes, about 23 minutes, about 24 minutes, about 25 minutes, about 26 minutes, about 27 minutes, about 28 minutes, about 29 minutes, or about 30 minutes. In one aspect, the period of time for the gelling solution to form gel is about 1 minute to about 10 minutes.

(d) Method of Preparing a Therapeutic Gel Composition

One aspect of the instant disclosure encompasses a method for preparing a therapeutic composition for oral administration of an active ingredient to an animal. The method comprises solubilizing an amount of a dry powder composition in a volume of solvent to form a gelling solution, concomitantly or subsequently mixing an active ingredient with the gel solution and allowing a period of time for the gelling solution to form a gel. In some aspects, the solvent is water. Accordingly, a method of the instant disclosure can comprise solubilizing an amount of a dry powder composition in a volume of water to form a gelling solution, concomitantly or subsequently mixing an active ingredient with the gel solution and allowing a period of time for the gelling solution to form a gel. In some aspects, a dose of the active ingredient is mixed with the solvent before mixing with the powder composition. In some aspects, a dose of the active ingredient is mixed with the powder composition before mixing with the solvent. In some aspects, a dose of the active ingredient is mixed with the solvent concomitantly with the powder composition. The powder composition can be as described in Section I herein above. The active ingredient and the therapeutic composition comprising the active ingredient can be as described in Section II herein above.

In one aspect of the method, solubilizing an amount of the dry powder composition in a volume of water to form a gelling solution comprises adding about 50 g to about 200 g of the dry powder in one liter of water. In one aspect, about 50 g, about 55 g, about 60 g, about 65 g, about 70 g, about 75 g, about 80 g, about 85 g, about 90 g, about 95 g, about 100 g, about 105 g, about 110 g, about 115 g, about 120 g, about 125 g, about 130 g, about 135 g, about 140 g, about 145 g, about 150 g, about 155 g, about 160 g, about 165 g, about 170 g, about 175 g, about 180 g, about 185 g, about 190 g, or about 200 g in one liter of water. In certain aspect, about 125 g to about 135 g of the dry powder is added to one liter of water.

In another aspect of the method, the gelling solution comprises about 1% (w/v) to about 50% (w/v) of dry powder composition. For example, the gelling solution can comprise about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), 31% (w/v), about 32% (w/v), about 33% (w/v), about 34% (w/v), about 35% (w/v), about 36% (w/v), about 37% (w/v), about 38% (w/v), about 39% (w/v), about 40% (w/v), about 41% (w/v), about 42% (w/v), about 43% (w/v), about 44% (w/v), about 45% (w/v), about 46% (w/v), about 47% (w/v), about 48% (w/v), about 49% (w/v), or about 50% (w/v). In one aspect, the gelling solution comprises about 10% (w/v) to about 15% (w/v) dry powder composition. In a specific aspect, the gelling solution comprises about 12% (w/v) dry powder composition. In an alternate aspect, the gelling solution comprises about 13% (w/v) dry powder composition.

The water used for preparing the gelling solution for the method of preparing a therapeutic gel composition may be water that is readily available in the farm, or that is regularly used as a drinking water for the livestock. In one aspect, water is cold water. For example, the water can be about 15° C., about 16° C., about 17° C., about 18° C., about 19° C., about 20° C., about 21° C., about 22° C., about 23° C., about 24° C., or about 25° C.

In further aspect of the method, a period of time for the gelling solution to form a gel may be about 10 minutes to about 30 minutes, 5 minutes to about 20 minutes, or about 1 minute to about 10 minutes. The period of time for gelling solution to form a gel can be about 1 minute, about 2 minutes, about 3 minutes, about 4 minutes, about 5 minutes, about 6 minutes, about 7 minutes, about 8 minutes, about 9 minutes, about 10 minutes, 11 minutes, about 12 minutes, about 13 minutes, about 14 minutes, about 15 minutes, about 16 minutes, about 17 minutes, about 18 minutes, about 19 minutes, about 20 minutes, 21 minutes, about 22 minutes, about 23 minutes, about 24 minutes, about 25 minutes, about 26 minutes, about 27 minutes, about 28 minutes, about 29 minutes, or about 30 minutes. In one aspect, the period of time for the gelling solution to form gel is about 1 minute to about 10 minutes.

In some aspects, the dry powder composition comprises a composition of Table 1. When the powder composition comprises a composition of Table 1, a method of the instant disclosure encompasses solubilizing the powder composition at a rate of about 125 g to about 135 g of the dry powder in one liter of water. In some aspects, the method comprises solubilizing about 400 to about 500 g in one gallon of water.

The amount of active ingredient present in the therapeutic composition can be optimized to achieve an effective dosage. An effective dosage may be determined based on factors such as the disease state, age, sex and weight of the animal to be treated.

Alternatively, the effective dosage may be determined by a veterinarian. Dosage regimens may be adjusted to provide the optimum therapeutic response. For example, a single dose may be administered, several divided doses may be administered over time, or the dose may be reduced or increased proportionally as indicated by the urgency of the treatment situation.

In one aspect, the active ingredient can be added at a volume of about 1 μl to about 500 ml, to about 0.1 ml to about 100 ml, or about 1 ml to about 10 ml. In various aspects, the active ingredient is added at about 1 μl, about 10 μl, about 100 μl, about 1000 μl, about 2 ml, about 3 ml, about 4 ml, about 5 ml, about 6 ml, about 7 ml, about 8 ml, about 9 ml, about 10 ml, about 15 ml, about 20 ml, about 25 ml, about 30 ml, about 35 ml, about 40 ml, about 45 ml, about 50 ml, about 55 ml, about 60 ml, about 65 ml, about 70 ml, about 75 ml, about 80 ml, about 85 ml, about 90 ml, about 95 ml, about 100 ml, about 125 ml, about 150 ml, about 200 ml, about 250 ml, about 300 ml, about 350 ml, about 400 ml, about 450 ml, about 500 ml, about 550 ml, about 600 ml, about 650 ml, about 700 ml, about 750 ml, about 800 ml, about 850 ml, about 900 ml, about 950 ml or about 1000 ml. In some aspects, the amount is about 200 μl.

In another aspect, the active ingredient is present in the therapeutic gel at about 0.01% (w/v) to about 5% (w/v). For example, the active ingredient is present in the therapeutic gel at about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6%

(w/v), about 0.7% (w/v), about 0.8% (w/v), about 0.9% (w/v), about 1% (w/v), about 2% (w/v), about 3% (w/v), about 4% (w/v), or about 5% (w/v), about 6% (w/v), about 7% (w/v), about 8% (w/v), about 9% (w/v), or about 10% (w/v).

(e) Method of Administering an Active Ingredient

Another aspect of the instant disclosure encompasses a method of orally administering an active ingredient to an animal. The method comprises preparing or having prepared a therapeutic gel composition comprising the active ingredient, and feeding the animal the gel composition, thereby administering the active ingredient to the animal. In some aspects, administering an active ingredient to the animal comprises feeding an effective amount of the gel composition to the animal. The therapeutic gel composition can be as described in Section III.

In some aspects, the animal is a pig. In some aspects, the gel composition comprises a composition of Table 1 solubilized at a rate of about 125 g to about 135 g of the dry powder in one liter of water. When the animal is a pig, a method of administering of the instant disclosure can comprise feeding the pig the gel composition at a rate shown in Table 2.

TABLE 2

| Age | Volume to scoop |
|---|---|
| Week 1 | 1 ounce (30 cc) per pig |
| Week 2 | 2 ounces (60 cc) per pig |
| Week 3 | 3 ounces (90 cc) per pig |
| Sows | 3 ounces (90 cc) per feeding |

In one aspect, the active ingredient is selected from the group consisting of a live vaccine, a probiotic, a prebiotic, an antibody protein, a targeted nutrient, a antiparasitic, a coccidiostat, a pain medication, a pheromone, and any combination thereof. In yet another aspect, the active ingredient is selected from the group consisting of toltrazuril, a *Lactobacillus* strain, meloxicam, a vaccine, and any combination thereof.

In some aspects, the active ingredient is a vaccine. When the animal is a pig, the vaccine can be a *Salmonella* spp. vaccine, an *E. coli* vaccine, an Erysipelas vaccine, a *Lawsonia* (ileitis) vaccine, or any combination thereof. In some aspects, the vaccine is an Erysipelas vaccine. In some aspects, the vaccine is a hemolytic *E. coli* vaccine. In some aspects, the active ingredient is toltrazuril. In other aspects, the active ingredient is a probiotic. In yet other aspects, the probiotic is a *Lactobacillus* strain.

(f) Method of Treating

One aspect of the instant disclosure encompasses a method of treating a disease in an animal. The method comprises administering a therapeutically effective amount of a composition of the instant disclosure to the animal.

As used herein, the terms "treating" or "treat" refer to arresting, inhibiting, correcting or attempting to arrest or inhibit or correct, the existence, development or progression of a disease and/or causing, or attempting to cause, the reduction, suppression, regression, or remission of a disease and/or a symptom thereof. As would be understood by those skilled in the art, various clinical and scientific methodologies and assays can be used to assess the development or progression of a disorder, and similarly, various clinical and scientific methodologies and assays can be used to assess the reduction, regression, or remission of a disorder or its symptoms. Similarly, "treatment" refers to both therapeutic treatment and prophylactic or preventative measures.

The term "therapeutically effective amount" as used with reference to the present formulation(s) and/or component(s) thereof as described herein refers to the quantity of the formulation(s) and/or component(s) thereof necessary to render the desired therapeutic result in an animal. For example, an effective amount is a level effective to treat, cure, or alleviate the symptoms of a disease for which the therapeutic formulation is being administered. Amounts effective for the particular therapeutic goal sought will depend upon a variety of factors including: the disease being treated and its severity and/or stage of development/progression; the bioavailability and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and, like factors well known to one of skill in the relevant art. Some variation in dosage will necessarily occur depending upon the condition of the animal being treated, and the veterinarian or other individual administering treatment will, in any event, determine the appropriate dosage for each individual animal.

The compositions can be as described in Sections I-III, the animals can be as described in Section IV(a), and the animal diseases can be as described in Section IV(b).

(g) Method of Controlling Behavior

Another aspect of the instant disclosure encompasses a method of controlling an animal's behavior. The method comprises administering to the animal a composition of the instant disclosure comprising a behavior-modifying semiochemical. For instance, a method of the instant disclosure can be a method of using a behavior-modifying semiochemical to calm an animal or to control reproduction. In some aspects, a method of the instant disclosure comprises a method of synchronizing estrus in a sow. The compositions can be as described in Sections I-III, the animals can be as described in Section IV(a), and the behavior-modifying semiochemical can be as described in Section III(b)(C).

(h) Method of Vaccinating

In an alternate aspect, the disclosure further encompasses a method of vaccinating an animal. The method comprises preparing a vaccine composition by solubilizing an amount of a dry powder composition in a volume of water to form a gelling solution. The method further comprises concomitantly or subsequently mixing a vaccine with the gel solution to form a vaccine composition and feeding the vaccine composition to the animal, thereby vaccinating the animal. In some aspects, vaccinating comprises feeding an effective amount of the vaccine composition to the animal. The powder composition can be as described in Section I herein above. In some aspects, the gel composition comprises a composition of Table 1.

The vaccine composition can comprise a *Salmonella* spp. vaccine, an *E. coli* vaccine, an Erysipelas vaccine, a *Lawsonia* (ileitis) vaccine, or any combination thereof. In one aspect, the animal may be a pig. When the animal is a pig, a method of administering can comprise feeding the pig the vaccine composition at a rate shown in Table 2.

Definitions

Unless defined otherwise, all technical and scientific terms used herein have the meaning commonly understood by a person skilled in the art to which this invention belongs.

The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements.

"About" is used to provide flexibility to a numerical range endpoint by providing that a given value may be "slightly above" or "slightly below" the endpoint without affecting the desired result. The term "about" in association with a numerical value means that the numerical value can vary plus or minus by 5% or less of the numerical value.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein "effective amount" is meant a sufficient amount of the compound to provide the desired regulation of a desired function, such as gene expression, antigen induced immune reaction, protein function, or a disease condition. As will be pointed out below, the exact amount required will vary from subject to subject, depending on the species, age, and general condition of the subject, the severity of the disease that is being treated, the particular agent used, its mode of administration, and the like. Thus, it is not possible to specify an exact "effective amount." However, an appropriate effective amount can be determined by one of ordinary skill in the art using only routine experimentation.

As various changes could be made in the above-described cells and methods without departing from the scope of the invention, it is intended that all matter contained in the above description and in the examples given below, shall be interpreted as illustrative and not in a limiting sense.

EMBODIMENTS

The following non-limiting embodiments provide illustrative examples of the disclosure, but do not limit the scope of the disclosure.

Embodiment 1

Provided herein is a powder composition for oral administration of an active ingredient to an animal, the composition comprising:

a gelling agent;

a gel activator;

an antioxidant;

a buffering agent; and an electrolyte.

Embodiment 2

The composition of Embodiment 1, wherein the gelling agent is agar, alginate, carrageenan, gum Arabic, ghatti, tragacanth, pectin, guar, Gelan, Carboxy Methylcellulose or locust bean gum, or any combination thereof.

Embodiment 3

The composition of Embodiment 1, wherein the gelling agent is alginate.

Embodiment 4

The composition of Embodiment 1, wherein the gel activator is dicalcium phosphate, calcium carbonate, calcium gluconate, calcium iodate, calcium oxide, calcium sulfate, or any combination thereof.

Embodiment 5

The composition of Embodiment 1, wherein the antioxidant is sodium thiosulfate.

Embodiment 6

The composition of Embodiment 1, wherein the buffering agent is phosphates, carbonates, citrates, tris buffers, and buffered saline salts (e.g., Tris buffered saline or phosphate buffered saline), or any combination thereof.

Embodiment 7

The composition of Embodiment 1, wherein the buffering agent is disodium phosphate, monopotassium phosphate, and sodium bicarbonate.

Embodiment 8

The composition of Embodiment 1, wherein the electrolyte is a salt of sodium, magnesium, potassium, calcium, chloride, phosphate, bicarbonate, or any combination thereof.

Embodiment 9

The composition of Embodiment 1, wherein the electrolyte is sodium chloride and potassium chloride.

Embodiment 10

The composition of Embodiment 1, wherein a dry blend of the composition comprises a composition of Table 1.

Embodiment 11

The composition of Embodiment 1, wherein the active ingredient is a live vaccine, probiotics, prebiotics, antibody proteins, targeted nutrients, or any combination thereof.

Embodiment 12

The composition of Embodiment 1, wherein the animal is a pig.

Embodiment 13

The composition of Embodiment 12, wherein the active ingredient is a vaccine and the vaccine is a *Salmonella* spp. vaccine, an *E. coli* vaccine, an Erysipelas vaccine, a *Lawsonia* (ileitis) vaccine, or any combination thereof.

Embodiment 14

Further provided is a gel composition for oral administration of an active ingredient to an animal, the composition comprising:

a dry powder composition comprising:
a gelling agent;
a gel activator;
an antioxidant;
a buffering agent; and
an electrolyte; and
water.

Embodiment 15

The gel composition of Embodiment 14, wherein the dry powder composition comprises a composition of Table 1.

Embodiment 16

The gel composition of Embodiment 15, wherein the gel composition comprises about 125 g to about 135 g of the dry powder in one liter of water.

Embodiment 17

A gel therapeutic composition for oral administration of an active ingredient to an animal, the composition comprising a gel composition of Embodiment 1 or Embodiment 14 and an active ingredient.

Embodiment 18

The therapeutic composition of Embodiment 17, wherein the active ingredient is a vaccine.

Embodiment 19

The therapeutic composition of Embodiment 17, wherein the animal is a pig.

Embodiment 20

The therapeutic composition of Embodiment 19, wherein the active ingredient is an Erysipelas vaccine.

Embodiment 21

The therapeutic composition of Embodiment 19, wherein the active ingredient is toltrazuril.

Embodiment 22

The therapeutic composition of Embodiment 19, wherein the active ingredient is a probiotic.

Embodiment 23

The therapeutic composition of Embodiment 22, wherein the probiotic is a *Lactobacillus* strain.

Embodiment 24

A vaccine composition for vaccinating an animal, the vaccine composition comprising a gel composition of Embodiment 1 or Embodiment 14 and a vaccine.

Embodiment 25

The vaccine composition of Embodiment 24, wherein the animal is a pig.

Embodiment 26

The vaccine composition of Embodiment 25, wherein the active ingredient is a *Salmonella* spp. vaccine, an *E. coli* vaccine, an Erysipelas vaccine, a *Lawsonia* (ileitis) vaccine, or any combination thereof.

Embodiment 27

The vaccine composition of Embodiment 25, wherein the vaccine is an Erysipelas vaccine.

Embodiment 28

A probiotic gel composition, the composition comprising a gel composition of Embodiment 1 or Embodiment 14 and a probiotic.

Embodiment 29

The probiotic composition of Embodiment 28, wherein the probiotic is a *Lactobacillus* strain.

Embodiment 30

The disclosure encompasses a method for preparing a therapeutic gel composition for oral administration of an active ingredient to an animal, the method comprising:

solubilizing an amount of a powder composition of Embodiment 1 or Embodiment 14 in a volume of water to form a gelling solution;
concomitantly or subsequently mixing an active ingredient with the gel solution; and
allowing a period of time for the gelling solution to form a gel.

Embodiment 31

The method of Embodiment 30, wherein the powder composition comprises a composition of Table 1.

Embodiment 32

The method of Embodiment 31, wherein the powder composition is solubilized at a rate of about 400 to about 500 g in one gallon of water or about 125 g to about 135 g of the dry powder in one liter of water.

Embodiment 33

A method of orally administering an active ingredient to an animal, the method comprising:
preparing or having prepared a therapeutic gel composition of claim 1 or any one of Embodiments 17, 24, or 28 using a method of Embodiment 30 further comprising an active ingredient; and
feeding the animal the gel composition, thereby administering the active ingredient to the animal.

Embodiment 34

The method of Embodiment 33, wherein the therapeutic gel composition comprises the gel composition of Embodiment 17.

Embodiment 35

The method of Embodiment 34, wherein the animal is a pig.

Embodiment 36

The method of Embodiment 34, wherein the animal is a pig, and the method comprises feeding the pig the gel composition at a rate shown in Table 2.

Embodiment 37

The method of Embodiment 33, wherein the active ingredient is toltrazuril.

Embodiment 38

The method of Embodiment 33, wherein the active ingredient is a probiotic.

Embodiment 39

The method of Embodiment 38, wherein the probiotic is a *Lactobacillus* strain.

Embodiment 40

A method of vaccinating an animal, the method comprising feeding the animal a vaccine composition of any one of Embodiments 24 to 27.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Probiotic Gel

The objective of this study is to determine the efficacy of providing an early colonizing bacterial probiotic applied to piglets during the lactation period in the form of an edible gel on piglet growth and productivity.

Treatments include a no product control and a *Lactobacillus* probiotic using Pig-E-Gel from Animal Science Products applied to sow crate floormats. Upon placement in the farrowing room, sows are allocated alternately to respective treatments while balancing parities. After the litter has been allowed to consume colostrum, the birth litter, pig number, gender, and cross-fostered litter (if applicable) are recorded. NOTE: cross-fostering is to only be performed within treatment and within the first 24 hours after birth.

The Pig-E-Gel is reconstituted with cold water prior to adding the probiotic, proportioned at a rate of about 12.5% by wt to about 13.5% by wt of the dry powder in one liter of water. Gel with probiotic is mixed fresh daily and any test material remaining at the end of the day will be discarded. The *Lactobacillus* probiotic will be provided as a powder and is kept refrigerated. One dose of the *Lactobacillus* probiotic ($1\times10^9$ CFU) is mixed per 10 mL of finished gel product. The *Lactobacillus* concentrate powder is mixed into water and added to the gel stock to provide the appropriate CFU for the day's application.

Gel containing the probiotic (10 mL/piglet to deliver a target dose of $1\times10^9$ CFU/piglet) is placed on the heating mats, targeting 10 mL/piglet on the day of farrowing for each sow assigned to the *Lactobacillus* treatment. This process is repeated on d 5 and d 15 post-farrowing.

Collected samples include 15 rectal swab samples from sows (same as sampled vaginally) at each farm site and 15 rectal swab samples from 15 pigs that are ~1 week prior to or close to weaning.

To select animals for each sample set of 15 to represent the sample group at each farm site sampling is distributed across multiple rooms and crate locations within each room as appropriate. There are ~270 sows/farrowing group at each farm site that will be at or around farrowing at the time of sampling. A total of 45 swabs/samples are obtained from each of the three farm sites.

During farrowing, sow ID, room #, farrow date, gestation length, parity, induction status(Y/N), and litter data/details are noted. During lactation, medication records, mortality, weaning date, number of pigs weaned/sow, pig/litter weaning weight are noted. For nursery pigs, treatment groups are kept together within the same pens; number pigs/pen, pen treatment, pig/pen weight in→out, mortality/removals. During Grow/Finish (if applicable), treatment groups are to be kept together within the same pens; number pigs/pen, pen treatment, pig/pen weight in→out, mortality/removals.

Example 2. Efficacy of Toltrazuril Administration Method of Via Pig-E-Gel™

Pig-E-Gel™ is a novel product to the marketplace, that provides a different mode of administration for drugs such as toltrazuril in suckling piglets. Traditionally, toltrazuril is administered to piglets individually via injection or oral administration. Use of a gel product administered at the litter level provides opportunity to apply a passive group treatment that requires minimal interaction with the piglets themselves. Gel application reduces piglet stress as well as decreases labor involved for administration. In addition, administering toltrazuril via a gel product in this study will inform the efficacy under commercial sow farm conditions.

The objective of this study is to compare efficacy of two administration methods of toltrazuril in suckling piglets with natural coccidia infection. Specific outcomes include Average daily weight gain, Crate-level coccidiosis diarrhea score, and Diarrhea-related sick pig percentages.

pigs alive at day 3, visual sow body condition score between 2-4 (criteria outlined in FIG. 1, Table 3), and the number of functional teats greater than or equal to the number of pigs alive at day 3.

TABLE 3

Scoring criteria

| Score | Condition | Detection of ribs, backbone, "H" bones, and "pin" bones |
|---|---|---|
| 1 | Emaciated | Obvious |
| 2 | Thin | Easily detected with pressure |
| 3 | Ideal | Barely felt with firm pressure |
| 4 | Fat | None |
| 5 | Overly Fat | None |

Eligible litters are randomly selected based on the quantities of each parity outlined in Table 4 and matched on the number of pigs, size of pigs (visual), sow parity, visual sow body condition, number of functional teats, room location and crate flooring materials (if applicable). The study occurs over 2 replicates. Quantities provided in parity breakdown in Table 4 are representative of 1 replicate. Each replicate encompasses 390 piglets, for a total of 780 piglets.

TABLE 4

Allocation quantities for one replicate

| | Control | | Toltrazuril Gel | | Ponazuril | | Forceris ™ | |
|---|---|---|---|---|---|---|---|---|
| | # litters | # piglets | # litters | # piglets | # litters | # piglets | # litters | # piglets |
| Parity 0 | 4 | 52 | 4 | 52 | 4 | 52 | 4 | 52 |
| Parity 1-2 | 3 | 39 | 3 | 39 | 3 | 39 | 3 | 39 |
| Parity 3-4 | 2 | 26 | 2 | 26 | 2 | 26 | 2 | 26 |
| Parity 5+ | 1 | 13 | 1 | 13 | 1 | 13 | 1 | 13 |
| Total | 10 | 130 | 10 | 130 | 10 | 130 | 10 | 130 |

Candidate herds have a history of clinical coccidiosis within 3-months of study initiation and provide an adequate number of sows to complete the study within 2 replicates back-to-back.

Clinical coccidiosis is established through clinical and diagnostic confirmation of coccidia within 3-months of the study beginning. Preliminary diagnostics on the candidate farm(s) include a full laboratory workup of clinical diarrhea in piglets >7 days of age. Fecal scoring of all litters with piglets >7 days of age is done to give a quantitative measure of scour prevalence. A minimum of 3 different litters with a scour prevalence of 20% or more of the piglets scoring 1 or higher on the scour score system described below (peak oocyte production occurs about 2-3 days after clinical signs develop) are selected for diagnostics. The diagnostic sample set includes pooled manure samples from the 3 different litters for fecal floatation analysis and each litter contributes a minimum of one sacrifice piglet for enterocolonic culture, rotavirus PCR, and a full histological tissue examination.

At approximately 3 days of age, litters that meet the following criteria are considered for enrollment: 13 or more Pigs are allocated by litter to treatment groups described in Table 5. In addition to treatment administration, on day 3, all piglets are individually tagged and weighed. Pigs from all treatment groups are processed (castrated and tail docked) on day 4 of age. Fostering of piglets is permitted, as required by farm management with the expectation that piglets are fostered within the same treatment group, if possible.

TABLE 5

Treatment groups (number of litters and number of piglets is for both replicates)

| Treatment | Description | # Litters | # Piglets |
|---|---|---|---|
| Control | Dexafer Iron injection* | 20 | 260 |
| Toltrazuril Gel | Pig-E-Gel & Toltrazuril∞ Mixture + Dexafer Iron injection¥ | 20 | 260 |
| Ponazuril | Pig-E-Gel & Ponazuril Mixture + Dexafer Iron injection | 20 | 260 |

TABLE 5-continued

| Treatment groups (number of litters and number of piglets is for both replicates) | | | |
|---|---|---|---|
| Treatment | Description | # Litters | # Piglets |
| Forceris ™ | Forceris ™ (gleptoferron and toltrazuril injection) | 20 | 260 |
| | Total | 80 | 1040 |

¥2 mL, 200 mg iron as ferric hydroxide in complex with a low molecular weight dextran fraction (Vetoquinol);
∞Toltrazuril product (dose to be determined) mixed with Pig-E-Gel ™ (Animal Science Products) will be applied to sow crate floor mats on day 3;
*Forceris ™ administered intramuscularly at 1 mL/pig Each individual sow and litter is monitored by the technicians daily. At any point throughout the study, the study monitor and attending veterinarian are notified by research site staff if any pigs are found to be showing unexpected and serious clinical signs. Veterinary staff conduct a visit per week to assess animal health and clinical signs. Assessors will be blinded to treatment group allocation.

A pooled fecal sample are collected from each crate when piglets are 7, 14, and 20 days of age. All samples are labeled by litter/sow ID and analyzed by fecal floatation. For cases with watery diarrhea, rectal swabs are collected and submitted for rotavirus PCR, culture, and sensitivity.

Growth—birth weaning and nursery performance. Piglets are weighed individually at 3 days of age (the day before processing), at weaning (~21 days of age), and end of nursery (6 weeks post-placement, ~63 days of age). When placed in the nursery, pigs are placed to allow for the same proportion of piglets from each treatment group within a pen.

Figure 2:
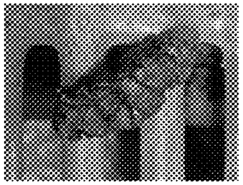
FIG. 2 is a series of photographs depicting crate-level scour score criteria. The score given for a crate is the most severe puddle in that crate.
Figure 2:
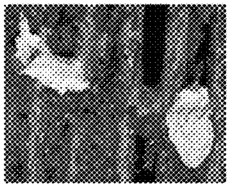
Figure 2:
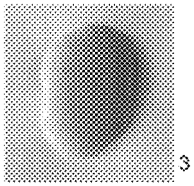
Figure 2:
Figure 2:
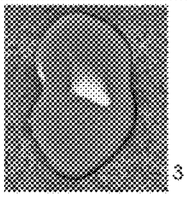

Crate-level coccidiosis scour score. Crates are assessed at 3 points in time when expected peak of clinical signs of coccidiosis (~7, 11 and 15 days of age). The scoring system used to evaluate scour is outlined in FIG. 2. The score is developed to encompass color and consistency of diarrhea throughout the crate and on the piglets themselves with characteristics specifically related to coccidiosis scour.

Individual piglet diarrhea-related sick pig score. On the same days as crate-level scour scoring, individual pigs are also assessed within each crate, to collect information on the percentage of scouring pigs. To be selected for further assessment, pigs must exhibit one of the three following criteria: dehydration (rough hair coat, sunken eyes, depression), poor gut fill (lack of stomach contents), or dirty perineum. If a pig meets the criteria, it is examined to determine whether it is scouring via abdominal palpation and expression of feces. If feces are a non-zero score, this animal is counted toward a total "diarrhea-related sick" pig count for that crate.

Data Analysis. To estimate the number of litters and pigs, an ideal data set is created in R (version 4.2.2). For crate level scores, simulated estimates are compared between Forceris™ and gel groups using a generalized mixed model (Poisson distribution) with treatment and replication as fixed effects and score day and crate as random effects. Twenty crates per treatment group is estimated to be the minimum number of crates required to secure power to detect a statistically significance difference assuming the total mean crate score difference will be ≥0.35. To determine if 20 crates per group would provide enough piglets when comparing ADG, it is assumed each sow produced 13 piglets. Simulated estimates is compared between Forceris™ and gel groups using a linear mixed model (gaussian distribution) with treatment as a fixed effect, parity, BCS, and litter size, and replication as covariates, and sow as a random effect. Twenty crates/group (or ~260 piglets/group) secures enough power to detect a statistically significant difference of ≥10 g in ADG between groups.

Descriptive statistics is conducted on sow variables measured (e.g., parity, litter size, #of functional teats, etc.,) and for all study outcomes (presence of oocytes over time. average daily weight gain, crate-level coccidiosis diarrhea score, diarrhea-related sick pig percentages). To test for differences between treated and control groups, the analysis plan for each outcome is detailed in Table 6. Statistical analysis will be completed using R statistical software. The statistical analysis plan for outcomes is detailed in Table 6. Presence of oocytes over time is described descriptively. Statistical analysis is completed using R statistical software.

TABLE 6

| Statistical analysis plan | |
|---|---|
| Outcome variable | Analysis |
| Crate-level coccidiosis scour score | Either generalized linear or ordinal mixed regression models adjusted by sow, parity, sow body condition, litter size, room, and replicate. |
| Individual piglet diarrhea-related sick pig score | Generalized logistic mixed regression models adjusted by start weight, sow, parity, sow body condition, litter size, room, number of functional teats, fostering, and replicate. |
| Individual piglet ADG | Generalized linear mixed regression models adjusted by start and end weight, start and end ages, sow, parity, sow body condition, litter size, room, number of functional teats, fostering, and replicate. |

The study timeline is shown in Table 7.

TABLE 7

| Study timeline | | |
|---|---|---|
| Study day | Piglet age | Event |
| 0 | ~3 days | Piglets enrolled day before processing<br>Individually tagged and weighed<br>Assigned treatments<br>Dexafer iron administered<br>Forceris administered |
| 1 | ~4 days | Piglets processed |
| 3 | ~6 days | Toltrazuril and Ponazuril Gel administered |
| 4 | ~7 days | Crate-level coccidiosis scour score<br>Individual diarrhea-related sick pig score |
| 11 | ~14 days | Crate-level coccidiosis scour score<br>Individual diarrhea-related sick pig score |

TABLE 7-continued

| Study timeline | | |
|---|---|---|
| Study day | Piglet age | Event |
| 17 | ~20 days | Crate-level coccidiosis scour score<br>Individual diarrhea-related sick pig score |
| 18 | ~21 days | Piglets individually weighed at weaning |

Mortalities, removals, individual injections. Individual pig treatments, mortalities and removals are recorded accordingly. Individual injectable treatment reasons are recorded daily. Cause of death and removal reasons are recorded, as well as fostering. If sample size allows, percentage of death, treated and removed pigs are compared using a generalized logistic mixed regression models adjusted by start weight, sow, parity, sow body condition, litter size, room, number of functional teats, fostering, and replicate (otherwise outcomes will be reported descriptively).

Adverse Events. As both treatments are approved products, the study veterinarian follows standard procedures for reporting any observed condition which is unintended, unfavorable, and occurs after administration of drug. Adverse events are reported to the study monitor immediately.

Pig-E-Gel™+toltrazuril mixing and administration: Pig-E-Gel™ is mixed as shown in Table 8. Pig-E-Gel™+ toltrazuril is administered to crate floor along with Dexafer Iron injection to piglets at 1 mL/pig.

TABLE 8

| Pig-E-Gel ™ + toltrazuril mixing and administration | | | | | |
|---|---|---|---|---|---|
| Toltrazuril dose target/2.5 kg pig | Total piglets treated | Total gel volume to prepare | Water | Baycox to add in water | Pig-E-Gel powder |
| 1 mL Baycox 5% (50 mg) | 1 | 30 mL per piglet (age ~4 d) | 29 ml | 1 ml | 4 g |
| | 260 | 7800 mL for 260 pigs | 7540 ml | 260 ml | 1026 g |
| Accounting for 10% overage | 1 | 33 mL per piglet (age ~4 d) | 32 ml | 1.1 ml | 4.4 g |
| | 10 | 330 mL per 10 piglets (age ~4 d) | 320 ml | 10.10 ml | 44 g |

Pig-E-Gel™+ponazuril mixing and administration: Pig-E-Gel™+ponazuril is administered to crate floor along with Dexafer Iron injection to piglets at 1 mL/pig. Marquis is mixed with water, then that homogenized mixture added with the gel is utilized (Table 9).

TABLE 9

| Pig-E-Gel ™ + ponazuril mixing and administration | | | | |
|---|---|---|---|---|
| Total gel volume administered per pig | Total piglets treated | Water | Marquis to add in water | Pig-E-Gel powder |
| 30 mL per piglet (age ~4 d) | 250 | 6.5 L | ¼ tube | 1000 g |
| | 500 | 13 L | ½ tube | 2000 g |
| | 1000 | 26 L | 1 tube | 4000 g |

Example 3. Oral Administration of Meloxicam in Pig-E-Gel™

Tail docking and castration, "processing," of young pigs is common in the swine industry to reduce aggression, tail biting and to inhibit boar taint. Currently, the US swine industry has not adopted pain mitigation during processing despite studies demonstrating that pigs present behavioral and physiological behaviors of pain. The main factors influencing this decision is the cost of pain control and additional labor needed to handle pigs a second time. This study evaluated the use of oral meloxicam, an inexpensive NSAID, on pain, average daily gain (ADG) and mortality at processing (5-7 days of age) using 2 different administration routes.

Materials and methods: The study was conducted on a 3,000 head sow farm in Iowa. Using parity 2 or 3 sows, 12 litters were selected and randomly assigned to one of the four treatments. Treatment 1 received an oral meloxicam gavage, treatment 2 received no treatment, treatment 3 received an oral gel/meloxicam mixture, and treatment 4 received only oral gel. Since the gel was green, treatments with no gel received green dye in the crate. Litters and video footage were randomly labeled to keep farm staff and scorers blinded. On day 1, 24 hours pre-processing (PP), pigs were weighed and marked with a number (1-15). On day 2, treatment 1 was administered (1 mL, 2.4 mg of compounded meloxicam, Veterinary Pharmaceutical Solutions) via oral drench 2 hours prior to processing. Treatment 2 was administered no treatment, but the mat was covered in green dye 2 hours prior to processing. Treatment 3 was administered 30 mL per pig of a compounded meloxicam/gel mixture (Pig-E-Gel, Animal Science Products) 3 hours prior to processing. The mixture contained 4.8 mg of meloxicam/piglet assuming a 50% consumption over 1 hour based on previous observations. Treatment 4 was given 30 mL of gel per pig 3 hours prior to processing. One caretaker performed processing procedures: tail-docking for both sexes and castration of males. Video recording was used to evaluate behaviors. Cameras were placed at the rear of each sow and pigs were observed three times by a blinded observer: 24 hours PP, immediately post-processing (IPP) and three hours post-processing (3PP). At each time point, pigs were scored using UNESP-Botucatu composite pain scale for assessing post-operative pain in piglets. Mortality was tracked and pigs were weighed at weaning. The primary variable was analyzed by a linear mixed model approach for repeated measures where the model considers the fixed effects of treatment, gender, time of observation and the interaction of treatment and time of observation as well as the random effect of pigs.

Figure 3:
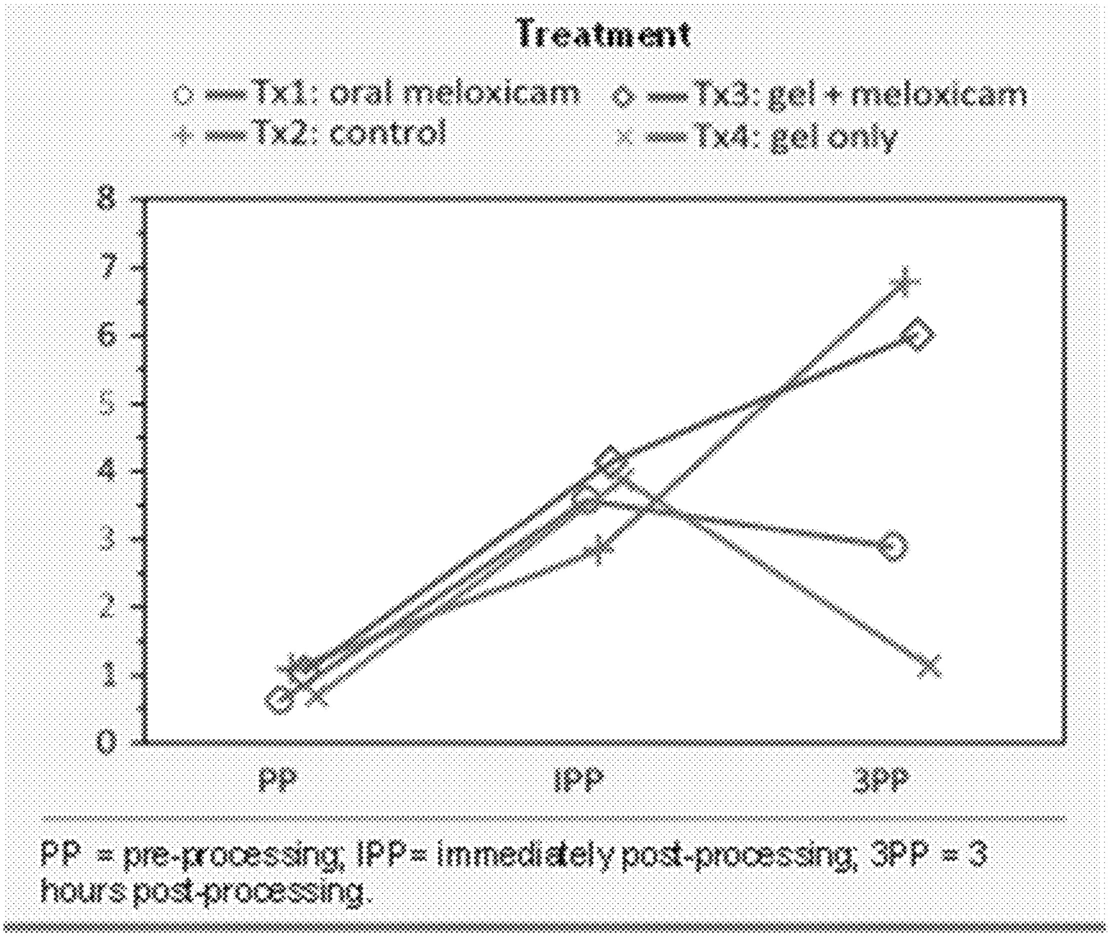
FIG. 3 is a line graph showing a comparison of pain scores of different treatment groups at three time points.

Results and discussion: There was an increase in pain score from PP to IPP and 3PP across all treatment groups verifying processing was a painful procedure (P-value<0.0001). All treatments had similar IPP scores indicating there was no effect on the immediate pain. This may suggest meloxicam administration needs to be earlier than 3 hours PP. However, there was a significant decrease in pain scores 3PP for treatments 1 and 4 respectively, providing evidence that utilizing oral meloxicam drench, an inexpensive NSAID, can decrease pain scores (FIG. 3). Treatment 4 was not a significant finding in lowering pain scores due to a low sample number (n=5) from exclusion of pigs sleeping. Gender of pigs plays a significant role with males having an average score of 1.42 points higher (P-value=0.0001) than females (more painful). No notable trends were found between treatments and ADG or mortality, further studies with an ideal sample power to identify the effects is warranted. Additional work is needed to increase consumption rate and better understand peak blood concentration, as pain scoring is a subjective measure.

Pig-E-Gel™+powdered meloxicam tablets mixing and administration: It was assumed each piglet eats 0.5 Tablespoon (7.5 mL) and weighed 1.8 kg. Target dosing=2.4 mg. 2.4 mg/7.5 mL=0.32 mg/mL meloxicam.

Meloxicam Tablets was 15 mg meloxicam per 180 mg tablet. (3785 ml)*(0.32 mg meloxicam/mL)*(180 mg powder/15 mg meloxicam)*(g/1000 mg)=14.53 g of meloxicam powder.

The meloxicam powder was mixed with the Pig-e-gel. Water was added to a 5 gallon pail. The combined powders were added to the water while stirring. The stirring was continued for 5 minutes. This mixing method does not account for the extra volume from the meloxicam tablets. Table 10A shows mixing of Pig-E-Gel™+powdered meloxicam tablets in different batch sizes.

TABLE 10A

Pig-E-Gel ™ + powdered meloxicam tablets mixing

| Size of Batch to make | | Pig-e-Gel | Weight of Meloxicam powder to add | Volume of water | Total Volume |
|---|---|---|---|---|---|
| Gallons | OZ | (grams) | (g) | to add | (mL) |
| 1 | 128 | 491 | 14.5 | 3785 | 3785 |
| 0.5 | 64 | 245 | 7.25 | 1892.5 | 1892.5 |
| 0.25 | 32 | 123 | 3.625 | 946.25 | 946.25 |

TABLE 10B

Meloxicam soluble (6 mg/mL) + Pig-e-gel ™ formulation

| Size of Batch to make | | Pig-e-Gel | Volume of Meloxicam soluble solution | Volume of water | Total Volume |
|---|---|---|---|---|---|
| Gallons | OZ | (grams) | to add (ml) | to add | (mL) |
| 1 | 128 | 491 | 200 | 3585 | 3785 |
| 0.5 | 64 | 245 | 100 | 1793 | 1893 |
| 0.25 | 32 | 123 | 50 | 896 | 946 |

It is assumed that each piglet eats 0.5 Tablespoon (7.5 mL) and weighs 1.8 kg. Target dosing=2.4 mg. 2.4 mg/7.5 mL=0.32 mg/mL meloxicam. Table 10B shows mixing of Pig-E-Gel™+soluble meloxicam in different batch sizes. For mixing, the meloxicam soluble is mixed with the water in a 5-gallon pail. While stirring the water, the Pig-e-Gel™ powder is added. Stirring is continued for 5 minutes.

Figure 4:
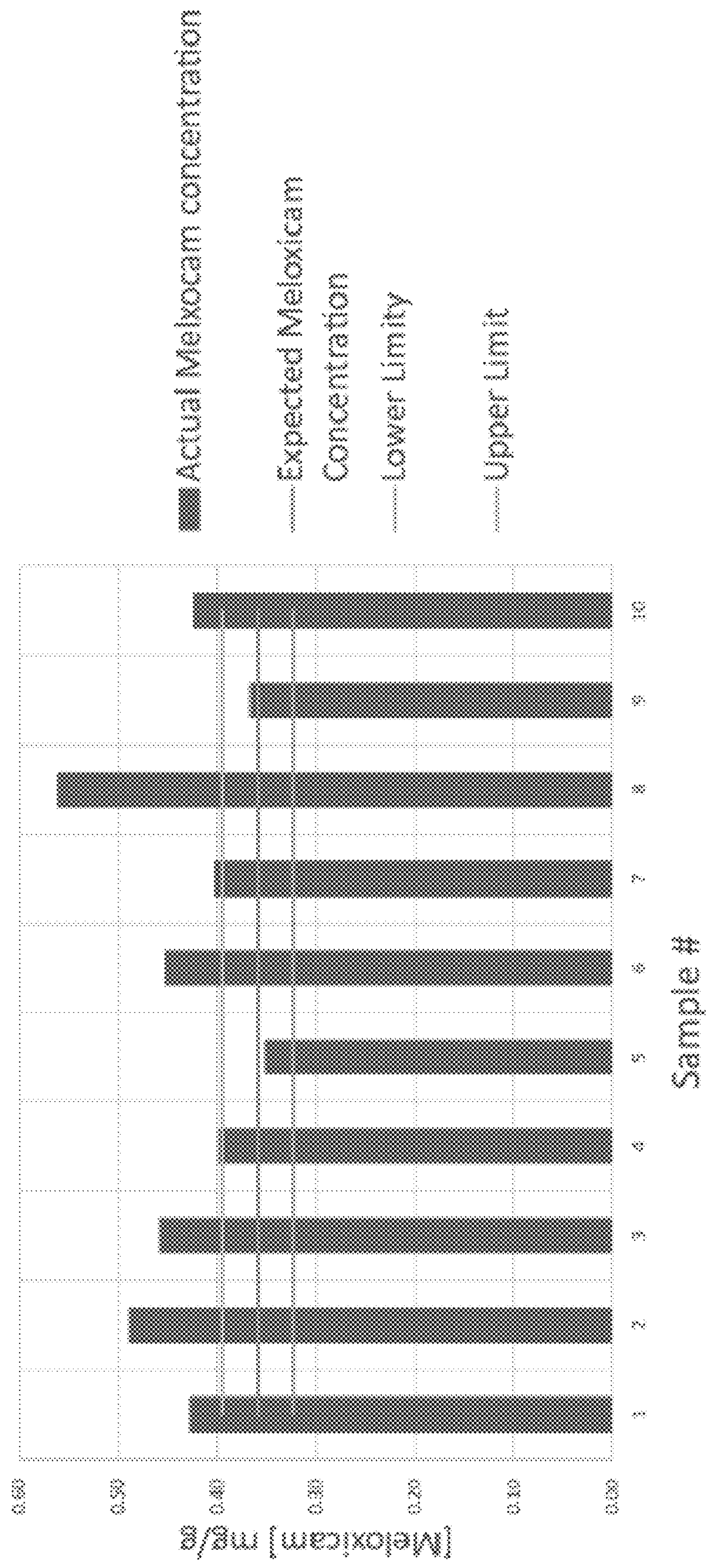
FIG. 4 is a bar graph depicting dosing of meloxicam in Pig-e-Gel™.
Figure 5A:
FIGS. 5A-5D are a series of photographs of different formulations of meloxicam. The formulations were prepared using methods provided in Tables 10A-10B.
Figure 5B:
Figure 5C:
Figure 5D:

Uniformity of dosing of meloxicam in samples prepared using Pig-e-Gel™ was examined. Target dosage of 0.36 mg/ml was expected in the samples prepared. As shown in FIG. 4, various samples prepared using Pig-e-Gel™ achieved the more than the target dosing amount of 0.36 mg/ml.

Further, different formulations pure, soluble, suspension and Pig-e-Gel™ prepared as described in Tables 10A-10B showed comparable properties (FIGS. 5A-5D).

Example 4. Pig-E Gel™+Avirulent *E. coli* for Farrowing Mat Use

Mixing and administration: In a clean plastic pail/vessel, 29 L of clean water is added. 1 L of *E. coli* bacterial culture is stirred to ensure the bacterial culture is evenly distributed. While stirring with a mixing paddle/stick, 4 kg of Pig-E-Gel™ powder is slowly added into the 30 L of liquid. The gel becomes firm for scooping within 10 minutes. The above mixture is enough for about 30 farrowing mats. 1 L (~34 oz) of the Pig-E Gel™/*E. coli* mixture is spread onto each farrowing mat for a litter of 12 to 14 piglets.

Example 5. Pig-E Gel™+Pheromones

This example details the formulation were prepared with Pig-E gel and maternal pheromones. Skatole and myristic acid are both present in pig feces. Previous research have found that piglets are attracted to these molecules. The goal of this example was these molecules to add it to the gel to attract piglets and improve consumption. Since both molecules are commonly found in pig farms, they present no risk to piglets. Table 11 shows non-surgical procedures used in administering and testing the formulation.

TABLE 11

Non-Surgical Procedures

| Procedure Name | Standard Procedure | Other Procedure Name |
|---|---|---|
| Ear Tag | | |
| Fecal - Free Catch | | |
| Other | | Fecal swab |
| Other 1 | | Color Identification |

Ear Tag: Piglets were ear tagged using commercially available ear tags. The experimenter restrained piglets and the tag was placed inside the ear avoiding blood vessels. Pigs were restrained during the procedure to ensure they do not move during the procedure. Appropriate equipment was used to tag the animals.

Fecal-Free Catch: Feces was collected from the farrowing crate after they defecate. There was no safety risk for the animal or experimenter.

Fecal swab: Piglets were restrained by the experimenter by placing one hand under their chest for support and holding them tightly against the experimenter's chest when doing the procedure to prevent any injury to the animal. Fecal samples were collected by introducing a swab in the animals' rectum.

Other 1: Piglets were marked with livestock markers of different colors to track individual pigs within a litter. Only commercially available livestock markers will be used. Pigs were marked on the back to prevent marker to affects ears, nose, or eyes.

Experimental agents used in the example are provided in Table 12. The dose and volume administered include 30 cc/pig as indicated by the manufacturer. The dosage included 300 Micro gram of Skatole and Myristic acid per 30 ml of gel. The formulation was administered as PO in the crate daily. The product was designed to efficiently deliver oral additives by voluntary feeding that might not otherwise be feasible via any source of drinking water or individual drench. The powdered gel components are food ingredients that are not sterilized but rather assayed by the manufacturer for microbiological wholesomeness prior to marketing.

TABLE 12

| Experimental agents | | | | |
|---|---|---|---|---|
| Agent Name | Other Agent Name | Class | Category | Pharma Grade? |
| Feed Additives | Pig-E-Gel | ABSL1 | Non-hazardous | No |
| Additives | Maternal Pheromone | ABSL1 | Non-hazardous | No |

The aims of this example were: 1. To confirm that 3-day old piglets consume the Pig-E-gel and 2. To evaluate if piglets have a preference for one of two different formulations of the gel. The control formulation used was the commercial product and the experimental formulation was the same formulation with the inclusion of the fecal maternal pheromone. For the purpose of this study, titanium dioxide (TiO2) was added as an undigestible marker to the gel. The presence of TiO2 in piglets' feces was used to confirm gel consumption. At 3 days of age, the farrowing crate was cleaned to remove piglets' feces and two mats or creep feeders were placed on each side of the farrowing crate. Each mat or feeder contained one of the two gel formulations (commercial vs. experimental) for a 24 h period. Pig-E-gel was be prepared as indicated by the manufacturer. Video cameras were installed on top of the farrowing crate to measure the amount of time piglets spent interacting with each formulation. Piglets will be marked with different colors and patterns on the back to try to follow individual pig behavior. After 24 hours, piglets' fecal samples were collected from the crate to determine the presence of TiO2 and confirmed consumption of the gel.

Although the chances of overconsumption of the gel were small, piglets were monitored for signs of salt toxicity for up to 48 h after the Gel was offered. Observations were conducted for any piglet showing signs of salt toxicity (e.g., aimless wandering, blindness, deafness, head pressing, "dog-sit", slowly raise their nose upward and backward, and fall on their side in spasms that may be followed by paddling of the legs).

Figure 6A:
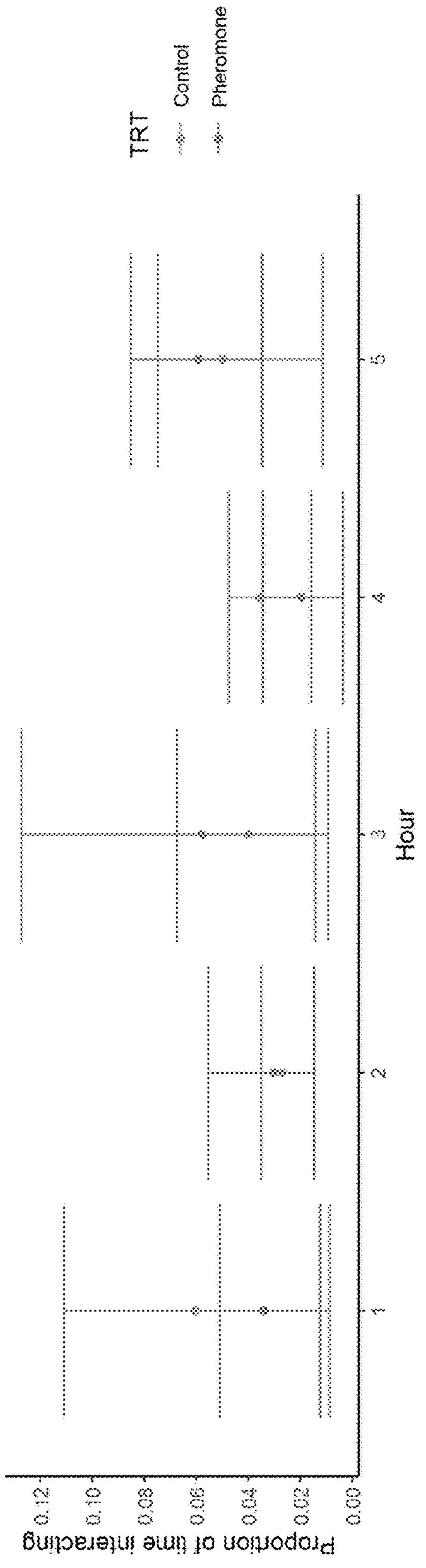
FIGS. 6A-6B are a dot graph proportion of time interacting (FIG. 6A) or time on mat (FIG. 6B) with Pig-E-Gel™ with or without pheromone on days 3, 4, and 5.
Figure 6B:
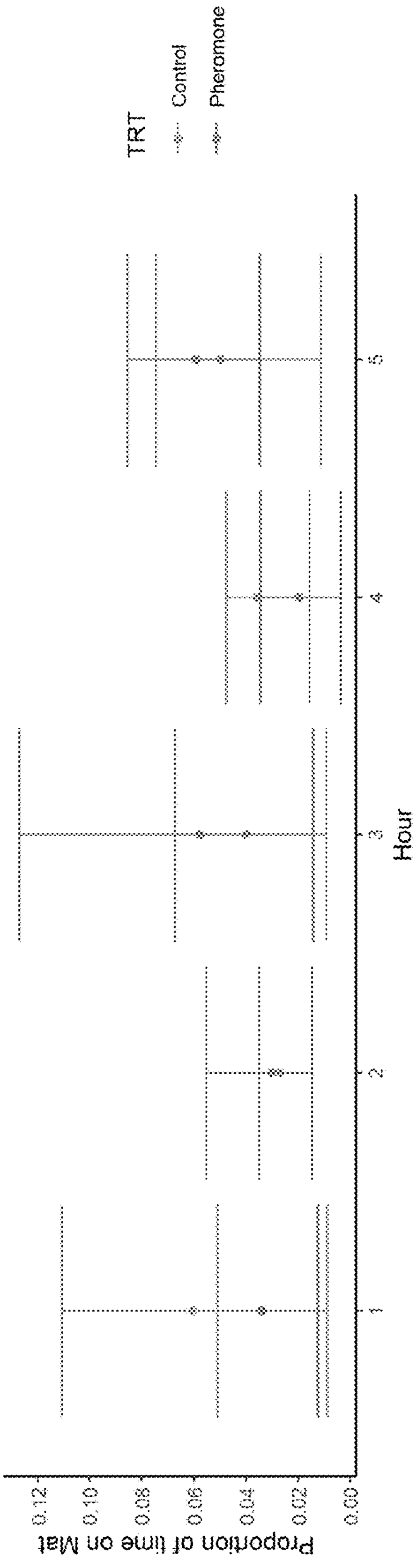

The proportion of time interacting or on the mat monitored over about 5 hours after administration of Pig-E Gel™ combined with pheromones are shown in FIGS. 6A-6B. As shown in FIGS. 6A-6B, Pig-E-Gel™ with pheromone increased the proportion of time interacting and time on mat as compared to the control.

SUMMARY

Pig-E-Gel™ dry powdered stabilizer mixes well with farm water and gels quickly to provide an ideal solution of hydrating nutrition while aiding the delivery of oral treatments including medications, live vaccines, and probiotics for piglets and sows in farrowing. This gel forms an excellent edible carrier for oral treatments for piglets and sows refusing feed. The carbohydrates in the gel also promote water uptake by intestinal cell. Gel ingredients include Calcium Sulfate, Water Stabilizers, Grain Products, Sodium Phosphate, Potassium Phosphate, Salt, Potassium Chloride, Sodium Bicarbonate, Artificial Flavoring and Artificial Coloring. To create the gel composition, 20 fl. oz (4 scoops) of Pig-E-Gel powder is thoroughly mixed with each gallon of cool clean water (or 500 grams of powder with 3.8 liters) to create a strong gelling solution. The gel is stirred for 1 minute to make a uniform solution that becomes firm for scooping within 10 minutes. The manufacturer recommended dose is about 30-90 cc of gel per pig. To deliver oral vaccines, probiotics, or other feed additives in Pig-E-Gel, dissolve the desired doses of the additive in the water portion before mixing with Pig-E-Gel to achieve uniform and rapid supplementation.

What is claimed is:

1. A method of vaccinating an animal, the method comprising:

a. preparing a vaccine composition by solubilizing an amount of a powder composition in a volume of water to form a gelling solution, wherein the powder composition comprises:
   i. a gelling agent;
   ii. a gel activator;
   iii. an antioxidant;
   iv. a buffering agent; and
   v. an electrolyte;
b. concomitantly or subsequently mixing a vaccine with the gel solution to form a vaccine composition, wherein the vaccine is selected from the group consisting of a *Salmonella* spp. vaccine, an *E. coli* vaccine, an Erysipelas vaccine, a *Lawsonia intracellularis* (ileitis) vaccine, and any combination thereof; and
c. feeding the vaccine composition to the animal, thereby vaccinating the animal.

2. The method of claim 1, wherein the animal is a pig.

3. The method of claim 1, wherein the gelling agent of the powder composition is sodium alginate.

4. The method of claim 1, wherein the gel activator of the powder composition is dicalcium phosphate, calcium carbonate, calcium gluconate, calcium iodate, calcium oxide, calcium sulfate, or any combination thereof.

5. The method of claim 1, wherein the antioxidant of the powder composition is sodium thiosulfate.

* * * * *